(12) United States Patent
Rezach

(10) Patent No.: US 11,627,992 B2
(45) Date of Patent: Apr. 18, 2023

(54) LOCKING-CAP MODULE AND CONNECTOR

(71) Applicant: Warsaw Orthopedic, Inc., Warsaw, IN (US)

(72) Inventor: William A. Rezach, Covington, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 147 days.

(21) Appl. No.: 17/167,734

(22) Filed: Feb. 4, 2021

(65) Prior Publication Data

US 2022/0192708 A1 Jun. 23, 2022

Related U.S. Application Data

(63) Continuation-in-part of application No. 17/128,615, filed on Dec. 21, 2020.

(51) Int. Cl.
*A61B 17/70* (2006.01)
*A61B 17/88* (2006.01)
*A61B 17/86* (2006.01)

(52) U.S. Cl.
CPC ...... *A61B 17/7001* (2013.01); *A61B 17/8695* (2013.01)

(58) Field of Classification Search
CPC ............ A61B 17/7001; A61B 17/7032; A61B 17/7035; A61B 17/7037; A61B 17/8695
USPC ....... 606/267, 270, 271, 272, 273, 274, 275, 606/278, 279, 104, 86 A
See application file for complete search history.

(56) References Cited

U.S. PATENT DOCUMENTS

| | | | |
|---|---|---|---|
| 6,540,749 B2 | 4/2003 | Schafer et al. |
| 6,641,586 B2 | 11/2003 | Varieur |
| 6,726,687 B2 | 4/2004 | Jackson |
| 6,730,089 B2 | 5/2004 | Jackson |
| 6,786,903 B2 | 9/2004 | Lin |
| 6,918,911 B2 | 7/2005 | Biedermann et al. |
| 7,141,051 B2 | 11/2006 | Janowski et al. |
| 7,156,850 B2 | 1/2007 | Kim |
| 7,204,838 B2 | 4/2007 | Jackson |
| 7,211,086 B2 | 5/2007 | Biedermann et al. |
| 7,223,268 B2 | 5/2007 | Biedermann |
| 7,503,924 B2 | 3/2009 | Lee et al. |
| 7,530,992 B2 | 5/2009 | Biedermann et al. |

(Continued)

*Primary Examiner* — Ellen C Hammond
*Assistant Examiner* — David C Comstock
(74) *Attorney, Agent, or Firm* — Fox Rothschild LLP

(57) ABSTRACT

A locking-cap module may include a locking-cap having a first connecting flange and a second connecting flange opposite the first connecting flange extending from a side surface of the locking-cap. The locking-cap may further include a first retaining rail and a second retaining rail opposite the first retaining rail. The locking-cap module may further include a set screw configured to engage with corresponding threads of the locking-cap. In some embodiments, the first connecting flange and second connecting flange are configured to engage with a connector such that the top surface of the locking-cap is flush with a top surface of the connector in an engaged position. In some embodiments, the set screw is initially coupled to the locking-cap by a pre-loaded connection. In some embodiments, a surgical tool is provided for rotating the locking-cap module into the engaged position.

18 Claims, 15 Drawing Sheets

(56) References Cited

U.S. PATENT DOCUMENTS

| | | |
|---|---|---|
| 7,645,294 B2 | 1/2010 | Kalfas et al. |
| 7,717,939 B2 | 5/2010 | Ludwig et al. |
| 7,776,067 B2 | 8/2010 | Jackson |
| 7,896,902 B2 | 3/2011 | Jeon et al. |
| 7,955,359 B2 | 6/2011 | Matthis et al. |
| 7,967,850 B2 | 6/2011 | Jackson |
| 7,972,364 B2 | 7/2011 | Biedermann et al. |
| 8,016,862 B2 * | 9/2011 | Felix ............... A61B 17/7038 606/268 |
| 8,025,680 B2 | 9/2011 | Hayes et al. |
| 8,034,086 B2 | 10/2011 | Iott et al. |
| 8,075,590 B2 | 12/2011 | Janowski et al. |
| 8,100,946 B2 | 1/2012 | Strausbaugh et al. |
| 8,123,784 B2 | 2/2012 | Biedermann et al. |
| 8,162,989 B2 | 4/2012 | Khalili |
| 8,172,876 B2 | 5/2012 | Janowski et al. |
| 8,221,469 B2 | 7/2012 | Zehnder et al. |
| 8,221,472 B2 | 7/2012 | Peterson et al. |
| 8,226,690 B2 | 7/2012 | Altarac et al. |
| 8,267,969 B2 | 9/2012 | Altarac et al. |
| 8,328,850 B2 | 12/2012 | Bernard et al. |
| 8,343,191 B2 | 1/2013 | Matthis et al. |
| 8,465,528 B2 | 6/2013 | Schumacher |
| 8,535,352 B2 | 9/2013 | Altarac et al. |
| 8,551,142 B2 | 10/2013 | Altarac et al. |
| 8,617,217 B2 | 12/2013 | Iott et al. |
| 8,679,162 B2 | 3/2014 | Strausbaugh et al. |
| 8,690,925 B2 | 4/2014 | Biedermann et al. |
| 8,740,946 B2 | 6/2014 | Peterson et al. |
| 8,784,455 B2 | 7/2014 | Matthis et al. |
| 8,870,927 B2 | 10/2014 | Matthis et al. |
| 8,888,820 B2 | 11/2014 | Blain et al. |
| 8,888,827 B2 | 11/2014 | Harper et al. |
| 8,911,478 B2 | 12/2014 | Jackson et al. |
| 8,920,470 B2 | 12/2014 | Ludwig et al. |
| 8,926,672 B2 | 1/2015 | Jackson et al. |
| 8,992,579 B1 | 3/2015 | Gustine et al. |
| 9,089,370 B2 | 7/2015 | Biedermann et al. |
| 9,131,962 B2 | 9/2015 | Cahill et al. |
| 9,144,437 B2 | 9/2015 | Matthis et al. |
| 9,144,444 B2 | 9/2015 | Jackson |
| 9,259,254 B2 | 2/2016 | Iott et al. |
| 9,271,760 B2 | 3/2016 | Biedermann et al. |
| 9,333,010 B2 | 5/2016 | Matthis et al. |
| 9,339,302 B2 | 5/2016 | Biedermann et al. |
| 9,358,046 B2 | 6/2016 | Nichols et al. |
| 9,439,682 B2 * | 9/2016 | Iott ................... A61B 17/7037 |
| 9,439,700 B2 | 9/2016 | Peterson et al. |
| 9,498,254 B2 | 11/2016 | Spratt et al. |
| 9,554,829 B2 | 1/2017 | Cahill et al. |
| 9,655,650 B2 | 5/2017 | Blain et al. |
| 9,655,652 B2 | 5/2017 | Biedermann et al. |
| RE46,431 E | 6/2017 | Jackson |
| 9,743,957 B2 | 8/2017 | Jackson |
| 9,782,204 B2 | 10/2017 | Spratt et al. |
| 9,848,918 B2 | 12/2017 | Strausbaugh et al. |
| 9,855,076 B2 | 1/2018 | Nichols et al. |
| 9,918,747 B2 | 3/2018 | Spratt et al. |
| 9,936,979 B2 | 4/2018 | Peterson et al. |
| 9,968,378 B1 | 5/2018 | Johnson et al. |
| 9,980,754 B2 | 5/2018 | Harper et al. |
| 10,004,541 B1 | 6/2018 | Jackson |
| 10,058,354 B2 | 8/2018 | Jackson et al. |
| 10,226,282 B2 | 3/2019 | Spratt et al. |
| 10,245,077 B2 | 4/2019 | Jackson |
| 10,245,078 B2 | 4/2019 | Jackson |
| 10,265,102 B2 | 4/2019 | Jackson et al. |
| 10,285,738 B1 | 5/2019 | Doubler et al. |
| 10,368,917 B2 | 8/2019 | Mishra et al. |
| 10,575,877 B2 | 3/2020 | Harper et al. |
| 10,603,081 B2 | 3/2020 | Harper et al. |
| 10,639,077 B2 | 5/2020 | Nichols et al. |
| 10,687,855 B2 | 6/2020 | Jackson et al. |
| 10,709,479 B2 | 7/2020 | Keyer et al. |
| 10,751,095 B2 | 8/2020 | Jackson |
| 2007/0118123 A1 | 5/2007 | Strausbaugh et al. |
| 2007/0167949 A1 * | 7/2007 | Altarac ............... A61B 17/7032 606/104 |
| 2007/0260246 A1 | 11/2007 | Biedermann |
| 2008/0183215 A1 | 7/2008 | Altarac et al. |
| 2008/0294202 A1 | 11/2008 | Peterson et al. |
| 2009/0062866 A1 * | 3/2009 | Jackson ............. A61B 17/7037 606/301 |
| 2009/0204155 A1 | 8/2009 | Aschmann |
| 2012/0239091 A1 | 9/2012 | Biedermann et al. |
| 2012/0283787 A1 | 11/2012 | Yuan et al. |
| 2013/0060294 A1 | 3/2013 | Donahue |
| 2013/0096618 A1 | 4/2013 | Chandanson et al. |
| 2014/0052190 A1 | 2/2014 | Biedermann et al. |
| 2014/0214084 A1 | 7/2014 | Jackson et al. |
| 2014/0350607 A1 | 11/2014 | Biedermann et al. |
| 2015/0119942 A1 | 4/2015 | Jackson et al. |
| 2017/0209178 A1 | 7/2017 | Cahill et al. |
| 2017/0303971 A1 | 10/2017 | Mishra et al. |
| 2018/0263665 A1 | 9/2018 | Yacoub et al. |
| 2019/0209213 A1 | 7/2019 | Spratt et al. |
| 2020/0205862 A1 | 7/2020 | Nichols et al. |
| 2020/0253644 A1 | 8/2020 | Biedermann |
| 2021/0298791 A1 * | 9/2021 | May ................... A61B 17/7037 |

* cited by examiner

LOCKING-CAP MODULE AND CONNECTOR

CROSS REFERENCE TO RELATED APPLICATIONS

This application is a continuation in part of U.S. patent application Ser. No. 17/128,615, titled LOCKING-CAP MODULE AND CONNECTOR, filed Dec. 21, 2020. The entire disclosure of which is incorporated herein by reference in its entirety. This application hereby incorporates the entire disclosure of each of U.S. patent application Ser. No. 16/830,377, titled POWERED MODULAR HEAD LOCKER, filed Mar. 26, 2020; U.S. patent application Ser. No. 17/118,694, titled HEAD POSITION AND DRIVER COMBINATION INSTRUMENT, filed Dec. 11, 2020; and U.S. patent application Ser. No. 17/167,258, titled INSTRUMENT FOR LOCKING ORTHOPEDIC SCREWS, filed Feb. 4, 2021.

FIELD

The present technology is generally related to locking modules including locking-caps and corresponding set screws configured to secure a longitudinal rod within a passageway of a connector and/or construct. Disclosed locking modules may utilize flanges that are nested within corresponding recesses of a connector and have an upper surface that is flush fit with an upper surface of the connector. Additionally, disclosed locking-caps may be initially coupled to a set screw by a preloaded connection configured to separate when the locking-cap is secured within a connector in an engaged position and the set screw advances towards a longitudinal rod to be secured, for example. Furthermore, once the preloaded connection is severed, an end user may reverse the set screw thereby binding the set screw to the locking-cap and enabling reverse rotation of the locking-cap to move the locking-cap to an non engaged position. In some embodiments, the locking module, locking-cap, and/or set screw may be secured to a patient vertebrae via a pedicle screw or the like, for example.

BACKGROUND

Conventional connectors may be secured to a patient vertebrae via a pedicle screw and include a passageway for securing a longitudinally extending rod. At least one type of connector may be referred to as a "tulip head" connector in the relevant art field. In order to secure the longitudinally extending rod to the connector, a set screw is typically used. Conventional set screws have an inherent limitation in that they may increase the height of the construct due to requiring a certain distance of threads to maintain sufficient mechanical clamping force on the longitudinal rod. For example, a set screw and connector may require a certain amount of engaged threads to sufficiently secure the longitudinal rod in the passageway of the connector and this type of fixation may adversely impact the height of the connector and the strength of a connection between the connector and an anchoring member.

SUMMARY

The techniques of this disclosure generally relate to a locking module having a locking-cap and set screw, for example. The locking module may be configured to retain a longitudinal rod within a passageway of a connector, for example. In some embodiments, the locking-cap mates with a corresponding connecting portion of the connector such that uppermost surfaces of flanges of the locking-cap are flush with adjacent top surfaces of the connector, for example. Additionally, in some embodiments, the locking-cap and set screw may be coupled together by a pre-loaded connection. For example, the locking-cap may be rotated into a engaged position with the connector by turning only the set screw due to the pre-loaded connection. After the locking-cap is positioned into the engaged position, an end user may continue turning the set screw and overcome the pre-loaded connection to advance the set screw and fully secure the longitudinal rod within the passageway of the connector. Additionally, in various embodiments the thread pattern of the set screw may include a run out portion that will bind with a corresponding counterbore portion of the locking-cap such that the locking-cap may be rotated into an un engaged position by reversing the set screw.

In one aspect, the present disclosure provides a locking-cap module. The module may include a locking-cap having an internal circumferential surface having a first thread pattern, and a first connecting flange and a second connecting flange opposite the first connecting flange, for example. In some embodiments, the first and second connecting flanges extend from a side surface of the locking-cap and define, at least partly, a top surface of the locking-cap, for example. The locking-cap may further include a first retaining rail and a second retaining rail opposite the first retaining rail, the first and second retaining rails may extend from the side surface of the locking-cap and define, at least partly, a bottom surface of the locking-cap, for example. The locking-cap module may further include a set screw having an external circumferential surface having a second thread pattern. The second thread pattern may correspond in size and shape to the first thread pattern for mating with the first thread pattern, for example. In some embodiments, the locking-cap may be configured to selectively couple with a connector in an engaged position, and when the locking-cap is in the engaged position, the first connecting flange and the second connecting flange engage with a connector such that an uppermost surface of the first connecting flange and an uppermost surface of the second connecting flange are generally flush with a top surface of the connector, for example.

In another aspect, the disclosure provides that the first locking edge may be engaged with a first stopping feature of the connector and the second locking edge may be engaged with a second stopping feature of the connector, for example.

In another aspect, the disclosure provides that the first connecting flange has a first slanted surface and the second connecting flange has a second slanted surface, and in the engaged position, the first slanted surface and the second slanted surface are disposed below the upper surface of the connector, for example.

In another aspect, the disclosure provides that the set screw and the locking-cap are initially coupled together by a pre-loaded connection, for example.

In another aspect, the disclosure provides that the pre-loaded connection may be configured to allow the locking-cap to be tightened into the engaged position by engaging and rotating the set screw, for example. Additionally, after the locking-cap is in the engaged position, the pre-loaded connection between the locking-cap and the set screw may be configured to break upon applying a sufficient rotational force to overcome the pre-loaded connection.

In another aspect, the disclosure provides that the first thread pattern has a counterbore and second thread pattern has a run-out-portion, for example.

In another aspect, the disclosure provides that the run-out-portion is further configured to maintain the set screw in an optimal position to capture and retain a longitudinal rod extending through a rod passageway of the connector, for example.

In another aspect, the disclosure provides for a locking-cap system. The locking-cap system may include a locking-cap having an internal circumferential surface having a first thread pattern, and a first connecting flange and a second connecting flange opposite the first connecting flange. The first and second connecting flanges may extend from a side surface of the locking-cap and define, at least partly, a top surface of the locking-cap, for example. The locking-cap may further include a first retaining rail and a second retaining rail opposite the first retaining rail, the first and second retaining rails may extend from the side surface of the locking-cap and define, at least partly, a bottom surface of the locking-cap, for example. The system may further include a set screw, the set screw may include an external circumferential surface having a second thread pattern, and the second thread pattern may correspond in size and shape to the first thread pattern for mating with the first thread pattern, for example. The system may further include a connector having an internal surface including a rod passageway and a connecting portion, for example. The connecting portion may be disposed proximate an upper surface of the connector and configured to selectively couple with the locking-cap such that the locking-cap is fixed relative to the connecting portion in a locked position, for example. In some embodiments, the connecting portion may include a first connecting channel and a second connecting channel opposite the first connecting channel, and the first connecting channel may be configured to connect with the first connecting flange and the second connecting channel may be configured to connect with the second connecting flange, for example. In some embodiments, the connecting portion may further include a third connecting channel and a fourth connecting channel opposite the third connecting channel, the third connecting channel may be configured to connect with the first retaining rail and the fourth connecting channel may be configured to connect with the second retaining rail, for example. In some embodiments, when in the engaged position, the first connecting flange and the second connecting flange engage with the connector such that an uppermost surface of the first connecting flange and an uppermost surface of the second connecting flange are generally flush with a top surface of the connector, for example.

In another aspect, the disclosure provides that the first connecting flange has a first locking edge and the second connecting flange has a second locking edge, and the connector has a first stopping feature and a second stopping feature, for example. Additionally, in some embodiments, the first stopping feature may be configured to engage with the first locking edge for preventing the locking-cap from rotating out of the engaged position and the second stopping feature may be configured to engage with the second locking edge for preventing the locking-cap from rotating out of the engaged position.

In another aspect, the disclosure provides for a surgical tool extending in a longitudinal direction and having a proximal end and a distal end, the proximal end having a drive end, and the distal end having a rotatable drive feature configured to engage with a drive cavity of the set screw, for example.

In another aspect, the disclosure provides that the distal end further comprises a plurality of mating protrusions, and the connector further comprises a plurality of mating cavities. In various embodiments, the plurality of mating protrusions may be configured to engage with the plurality of mating cavities for providing a counter-torque to the locking-cap, for example.

In another aspect, the disclosure provides that the distal end further comprises a plurality of arms and a plurality of mating rails, and the connector further comprises a plurality of lateral sidewalls and a plurality of mating channels, for example Additionally, the plurality of arms may be configured to engage with the plurality of lateral sidewalls for providing a counter-torque to the connector, and the plurality of mating rails may be configured to engage with the plurality of mating channels for providing a counter-torque to the connector, for example.

In another aspect, the disclosure provides that the set screw and the locking-cap may be initially coupled together by a pre-loaded connection, for example.

In another aspect, the disclosure provides that the pre-loaded connection may be configured to allow the locking-cap to be tightened into the engaged position by engaging and rotating the set screw, and break when a sufficient rotational force is applied to the set screw when the locking-cap is in the engaged position, for example.

In another aspect, the disclosure provides that the first thread pattern may include a run-out-portion and the second thread pattern may include a counterbore.

In another aspect, the disclosure provides that the locking-cap system may further include a longitudinal rod, a crown, and an anchoring member, for example. The connector may be secured to the anchoring member and the longitudinal rod may extend through the rod passageway, for example. The crown may facilitate positioning of the longitudinal rod in the rod passageway, and the run-out-portion may be configured to maintain the set screw in an optimal position to capture and retain the longitudinal rod with an optimal force, for example.

In another aspect, the disclosure provides a method for engaging a two piece locking-cap module with a connector. The method may include the step of providing a locking module comprising a locking-cap and a set screw, and the set screw may be operably coupled with the locking-cap by a preloaded connection, for example. The locking-cap may include a first connecting flange and a second connecting flange opposite the first connecting flange, the first and second connecting flanges may extend from a side surface of the locking-cap and define, at least partly, a top surface of the locking-cap, for example. The locking-cap may further include a first retaining rail and a second retaining rail opposite the first retaining rail, the first and second retaining rails may extend from the side surface of the locking-cap and define, at least partly, a bottom surface of the locking-cap, for example. The method may further include the step of providing a connector, and the connector may include an internal surface comprising a rod passageway and a connecting portion, for example. The connecting portion may be disposed proximate an upper surface of the connector and be configured to couple with the locking-cap such that the locking-cap is fixed relative to the connecting portion in a engaged position, for example. The connecting portion may include a first connecting channel and a second connecting channel opposite the first connecting channel, and the first connecting channel may be configured to connect with the first connecting flange and the second connecting channel may be configured to connect with the second connecting flange, for example. The connecting portion may further include a third connecting channel and a fourth connecting channel opposite the third connecting channel, the third connecting channel may be configured to connect with the first retaining rail and the fourth connecting channel may be configured to connect with the fourth retaining rail, for example. The method may further include the step of providing a surgical tool having a proximal end including a drive end and a distal end including a rotatable drive feature, for example. The method may further include the step of engaging the drive feature with a drive cavity of the set screw, for example. The method may further include the step of rotating the locking-cap module, via the drive cavity of the set screw, into the engaged position thereby fixing the locking-cap relative to the connector such that an upper surface of the first connecting flange and an upper surface of the second connecting flange are generally flush with corresponding upper surfaces of the connector, respectively, for example. The method may further include the step of rotating the set screw, after the locking-cap is fixed relative to the connector, with sufficient force to overcome the pre-loaded connection.

In another aspect, the disclosure provides for a method including the installation of an anchoring member in a boney structure of a patient, and securing the connector to the anchoring member, for example. The method may further include the steps of positioning a crown within the connector and positioning a longitudinal rod within a rod passageway of the connector on top of the crown, for example. The method may further include the step of rotating the set screw, after overcoming the pre-loaded connection, thereby securing the longitudinal rod with the rod passageway, for example.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

A locking-cap for securing a connector to a longitudinal rod and a pedicle screw is disclosed. The locking-cap may include a pair of connecting flanges and a pair of retaining rails that are configured to be retaining within corresponding retaining channels of a connector. Additionally, the locking-cap may include a pair locking edges that secure the locking-cap in an engaged position relative to the connector. Furthermore, the pair of locking flanges may engage with the connector at a connecting portion of the connector such that the top surface of the locking-cap is flush with the top surface of the connector in the engaged position. In some embodiments, the locking-cap may be initially coupled to a set screw by a pre-loaded connection. At least one object of the present disclosure is to provide a connector having an overall height that is relatively less than other connectors due to the particular geometry and structural features of the locking-cap.

Figure 1:
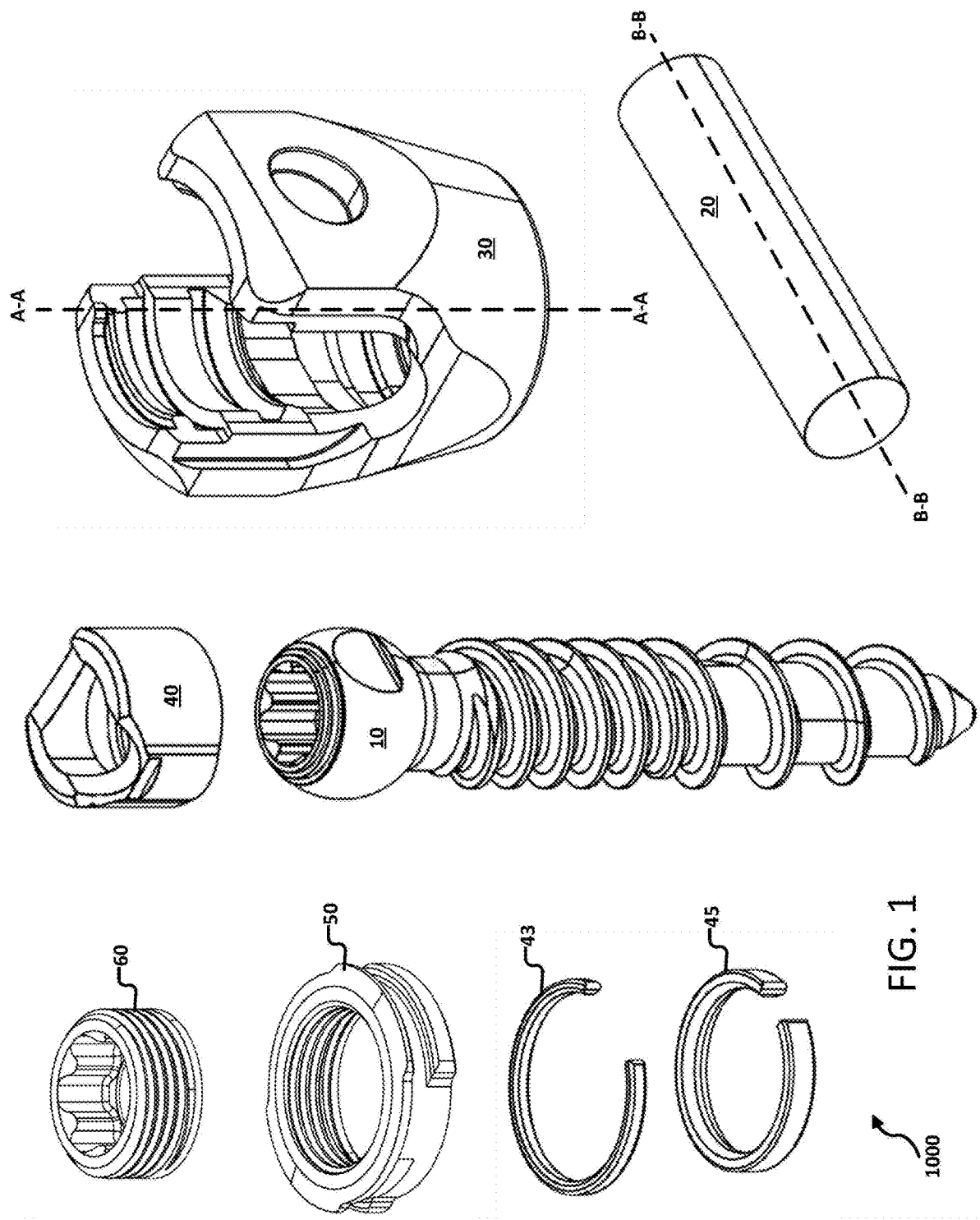
FIG. 1 is an exploded parts diagram of example components of a locking-cap system including a connector and an anchoring member.
Figure 2:
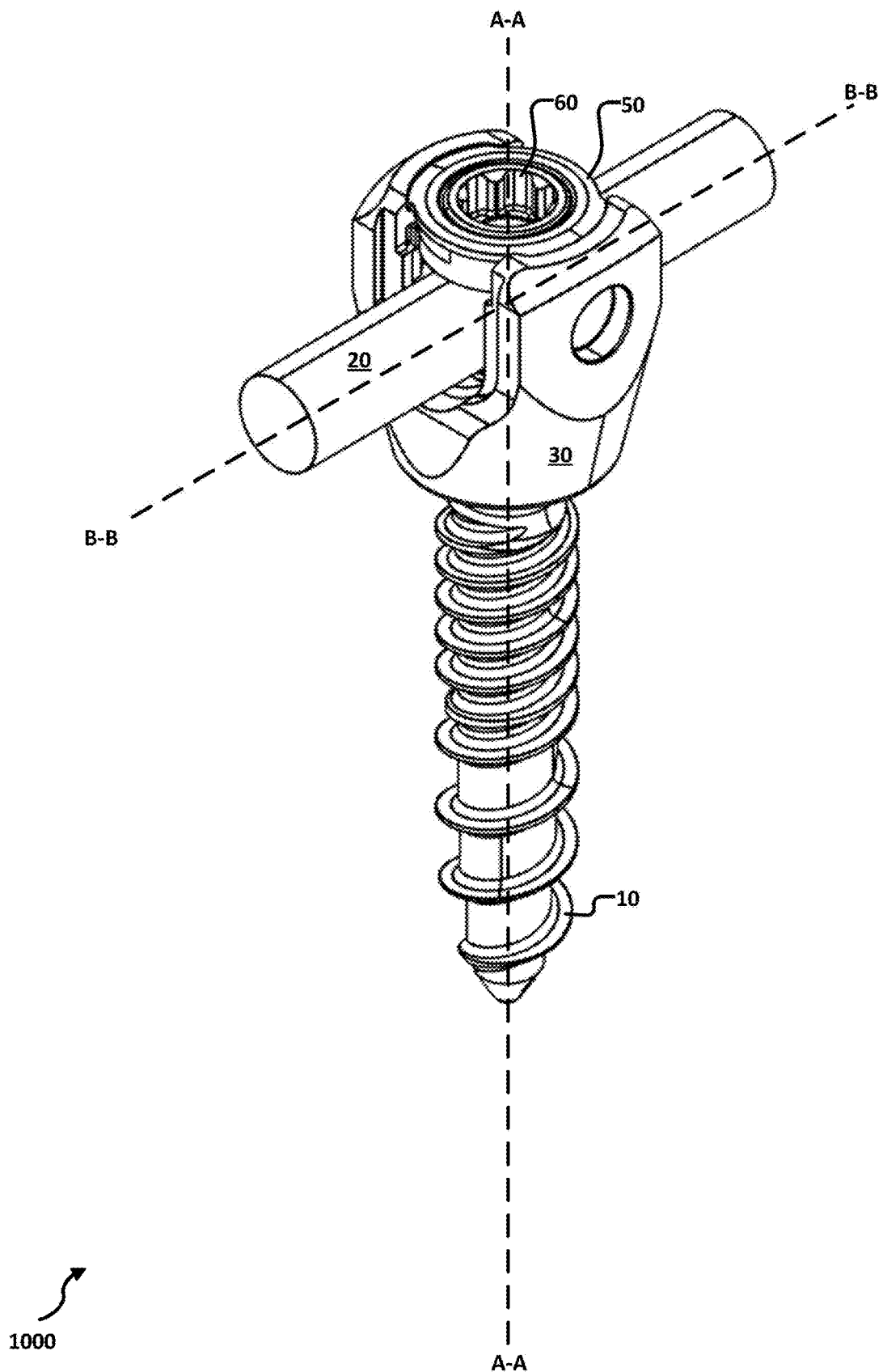
FIG. 2 is an assembled parts perspective view of an example locking-cap system including a connector and an anchoring member.

FIG. 1 is an exploded parts diagram of example components of a locking-cap system 1000. The locking-cap system 1000 may include a locking-cap 50, a crown 40, a set screw 60, a connector 30, a longitudinal rod 20, and an anchoring member 10. FIG. 2 is an assembled parts perspective view of an example locking-cap system 1000. In the illustrated embodiment, a set screw 60 may be positioned within an internal receiving cavity of a connector 30, for example. A crown 40 may be positioned over the head portion of the anchoring member 10 in axial alignment with a first axis A-A defined by the connector 30. The anchoring member 10 may be a pedicle screw, a multi axial screw, or a uniaxial screw, for example. Similarly, crown 40 may be any suitable type depending on the particular type of anchoring member 10. For example, the crown 40 may be configured for use with a multi axial screw (anchoring member 10) or configured for use with a uniaxial screw (anchoring member 10). In various embodiments, washer 43 and washer 45 may also be used to secure the head of anchoring member 10 within a bottom portion of connector 30

In practice a surgeon may install anchoring member 10 into a bone structure such as a patient vertebrae, for example. In various embodiments, anchoring member 10 may be secured to a bottom portion of connector 30 by a surgical instrument. For example, by pushing down on the connector 30 or crown 40 washer 43 and washer 45 may be seated within a bottom portion of connector 30 thereby securing the head of anchoring member 10 to connector 30. Several example tools and configurations consistent with this type of coupling are described in each of U.S. patent application Ser. No. 16/830,377, titled POWERED MODULAR HEAD LOCKER; U.S. patent application Ser. No. 17/118,694, titled HEAD POSITION AND DRIVER COMBINATION INSTRUMENT; and U.S. patent application Ser. No. 17/167,258, titled INSTRUMENT FOR LOCKING ORTHOPEDIC SCREWS. The contents of each are incorporated herein in entirety.

In various embodiments, the anchoring member 10 may extend through an internal receiving cavity of connector 30 into the boney structure such that the connector 30 may be positioned over and around the head of anchoring member 10. The surgeon may also install the crown 40 over the head portion of anchoring member 10. The crown 40 may be axially aligned with axis A-A of the connector. Next, a surgeon may insert a longitudinal rod 20 into a rod passageway of the connector 30. The rod 20 and connector 30 may be further positioned with respect to anchoring member 10 by the use of a reduction instrument (not illustrated), for example. The rod 20 may define an axis B-B and when the rod 20 is installed within the rod passageway of the connector 30, the rod may extend in a direction that is substantially perpendicular to axis A-A (at least for the portion of rod 20 within the connector 30). Next, a surgeon may secure the rod 20 with respect to the connector 30 by installing a locking-cap module 100. Locking-cap module 100 (see FIG. 4A) may include the locking-cap 50 and the set screw 60. In some embodiments, the set screw 60 may be initially coupled to the locking-cap 50 by a pre-loaded connection, for example. Further details of the locking-cap system 1000 will be discussed below, e.g., further discussion regarding the installation of the locking-cap 50 and set screw 60 relative to the connector 30 are discussed below with respect to FIGS. 6A-10. Additionally, an example surgical tool for tightening set screw 60, loosening set screw 60, and providing a counter torque to connector 30 is disclosed with reference to FIGS. 12A-14.

Figure 3A:
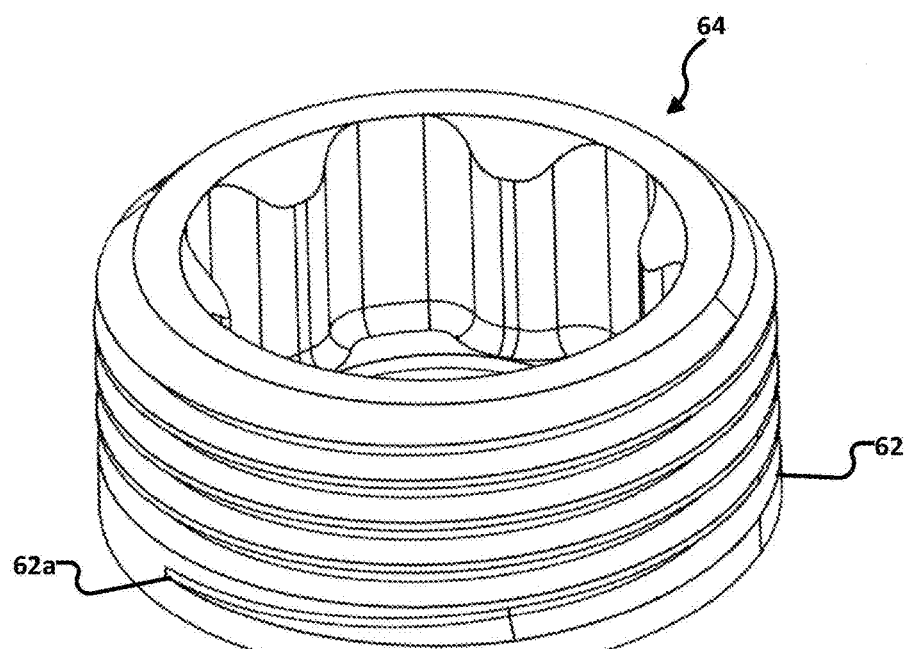
FIG. 3A is a perspective view of an example set screw.
Figure 3B:
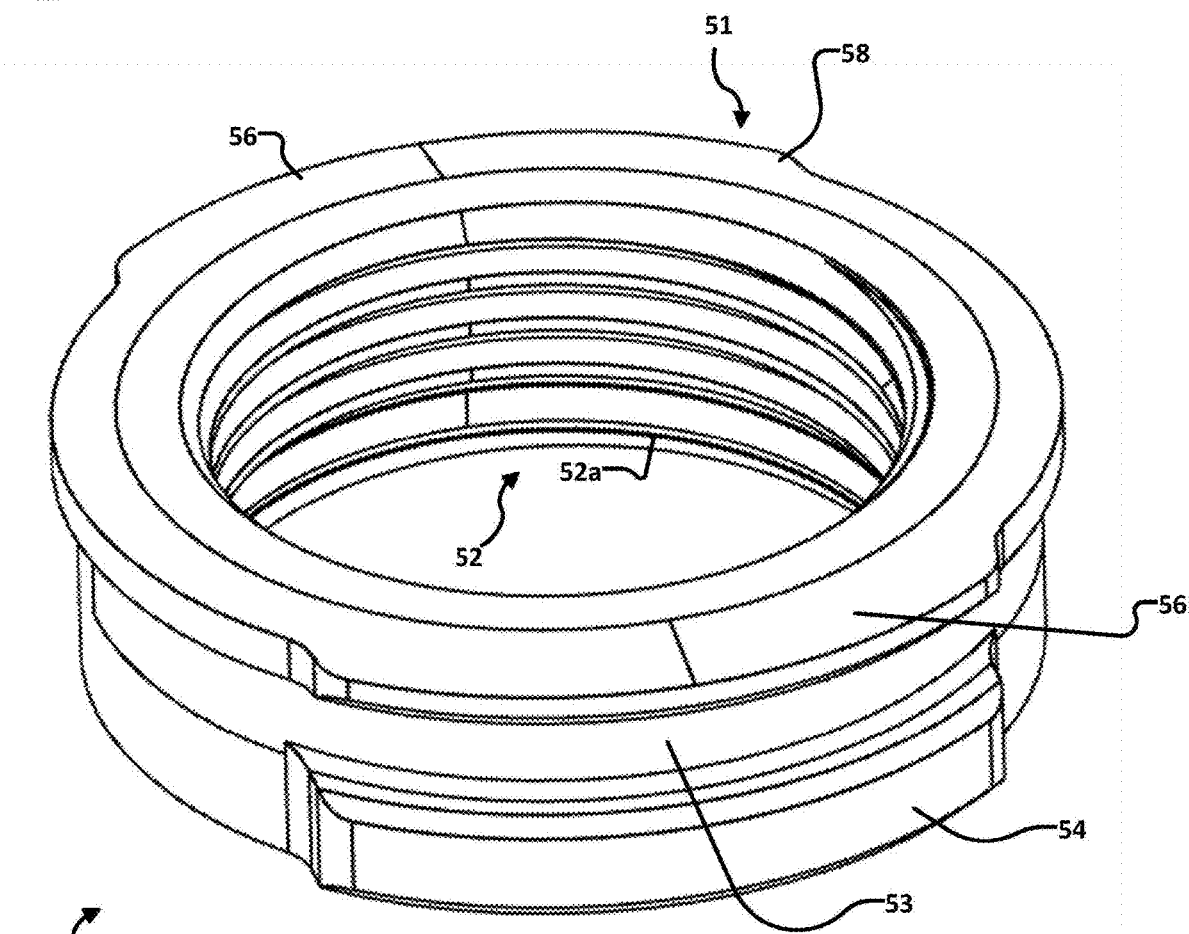
FIG. 3B is a perspective view of an example locking-cap.

FIG. 3A is a perspective view of an example set screw 60 and FIG. 3B is a perspective view of an example locking-cap 50. In the illustrated embodiment, set screw 60 may include a thread pattern 62 on an external circumferential surface thereof. In various embodiments, thread pattern 62 may have a run out portion 62a at a lower region of set screw 60 and on an external circumferential surface thereof. In various embodiments, set screw 60 may include a bump, hemispherical protrusion, conical protrusion, and/or a dimple 65 on the underside thereof serving as a contact point between the set screw 60 and a longitudinal rod 20 (see FIGS. 4B and 10). The set screw 60 may also include a drive cavity 64, that is accessible to a surgical tool having a corresponding drive feature 202 (see FIG. 12B) from a top portion of the set screw 60, for example. In the illustrated embodiment, drive cavity 64 may be configured for a hexalobular head driver, although other designs are contemplated. For example, drive cavity 64 may resemble the geometry of the tip of a torx driver, hex driver, phillips driver, square head driver, hexalobular driver, polygonal driver, or the like. In various embodiments, a size and shape of drive cavity 64 may correspond to a size and shape of drive feature 202.

Locking-cap 50 may include an opening 51 exposing an internal sidewall surface having a thread pattern 52, for example. In various embodiments, thread pattern 52 may have a counterbore 52a at a bottom portion thereof, for example. Counterbore 52a may have a size, shape, and/or structure configured to bind to the run out portion 62a such that when reversing set screw 60 the locking-cap 50 may also be rotated.

In various embodiments, the opening 51 and thread pattern 52 may be configured to receive set screw 60 therein. For example, the size of the set screw 60 corresponds to the size of the opening 51 and the threads of thread pattern 62 of the set screw correspond to the threads of thread pattern 52 of the locking-cap. The locking-cap 50 may include a plurality of connecting flanges 56, for example. In the illustrated embodiment, a pair of connecting flanges 56 is shown and top surfaces of the connecting flanges may be flush, substantially flush, and/or partially flush, with a top surface of the connector 30 in an installed and engaged position. Other embodiments may include additional connecting flanges 56, for example three or four connecting flanges depending on the chosen design. Connector 30 may further include at least one locking edge 58 defining an end portion adjacent to a corresponding connecting flange 56. The locking edge 58 may take any suitable shape and in the illustrated embodiment locking edge 58 is shaped like a curved outdent extending laterally from a side surface flanges 56, for example. In the illustrated embodiment, an upper surface of connector 30 may be defined, at least partly, by flanges 56 that extend laterally from side surfaces of the connector 30. In plane view, the flanges 56, and locking edge 58 define, at least partly, a portion of the perimeter of the top surface of locking-cap 30, for example. Similarly, the flanges and locking edge are flush with a top surface of connector 30. For example, top surfaces of the connector 30, flanges 56, and locking edge 58 are coplanar or substantially coplanar.

Connector 30 may further include a plurality of retaining rails 34, for example. In the illustrated embodiment, a pair of retaining rails 34 is shown extending laterally from an outside side surface of connector 30 adjacent a bottom portion of connector 30 as an example Other embodiments may include additional retaining rails 34, for example, three or four retaining rails 34 depending on the chosen design. Additionally, retaining rails 34 may have a varying cross-sectional height and/or thickness. For example, in some embodiments, retaining rail 34 may be thickest nearest the flat portion of the side surface of connector 30 (nearest a center of connector 30) and gradually thin out approaching the vertical sidewall surface of the corresponding retaining rail 34. In the disclosed embodiment, in plane view, the connecting flange 36 and locking edge 38 are disposed above a corresponding retaining rail 34 and define, therebetween, a smooth sidewall portion that is recessed relative to the outermost side surfaces of the connecting flange 36 and retaining rail 34. For example, connector 30 may include a smooth recessed portion 33 spaced between and defined by, at least partly, a corresponding connecting flange 36 and retaining rail 34.

Figure 4A:
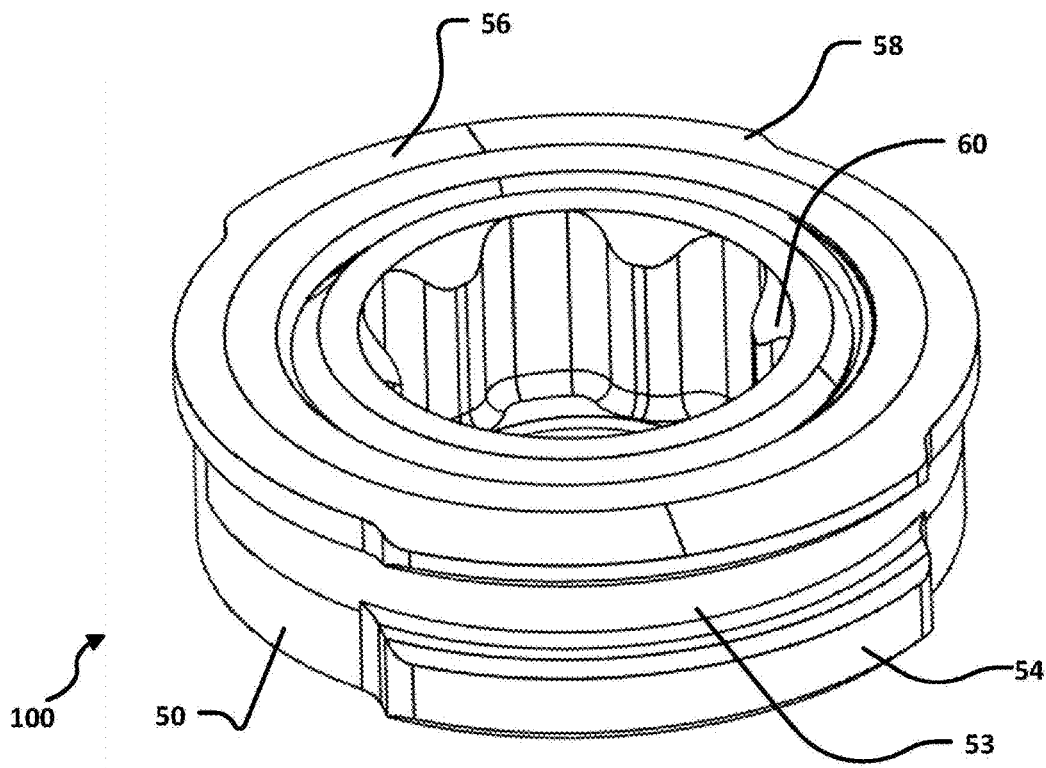
FIG. 4A is a perspective view of a pre-assembled locking-cap and set screw.
Figure 4B:
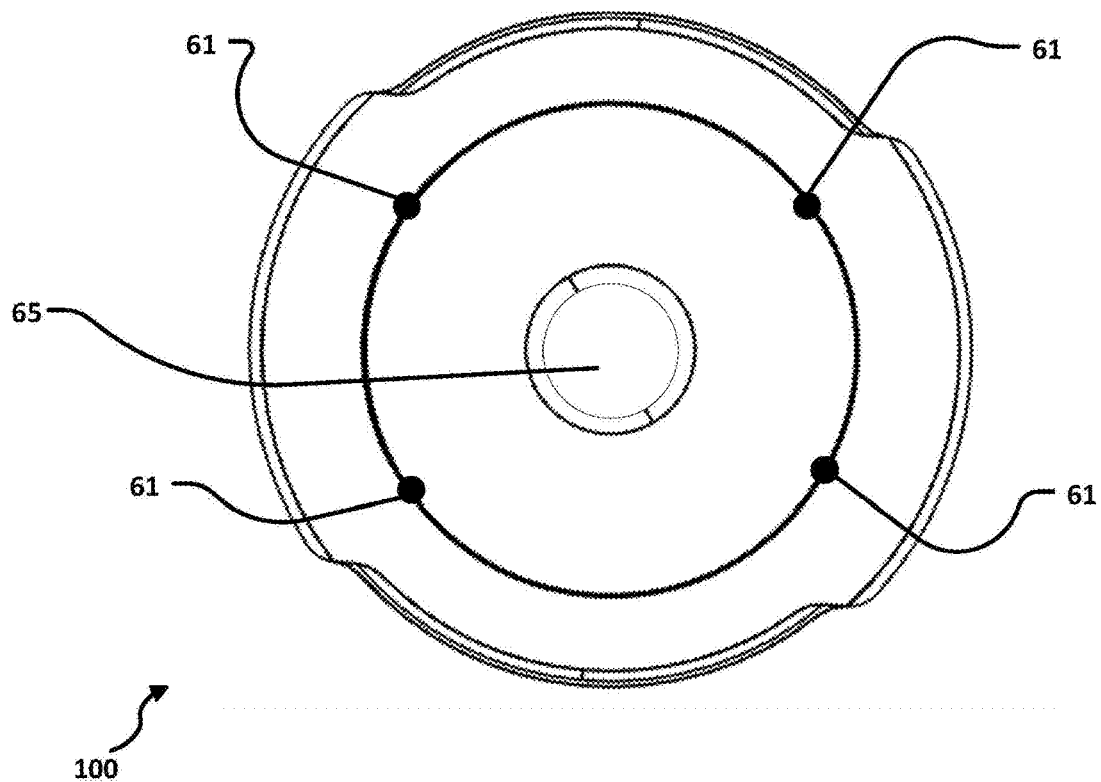
FIG. 4B is a top down view of a bottom portion of a pre-assembled locking-cap and set screw.

FIG. 4A is a perspective view of a pre-assembled locking-cap module 100, including a locking-cap 50 and a set screw 60. FIG. 4B is a top down view of a bottom portion of a pre-assembled locking-cap module 100 including a locking-cap 50 and set screw 60 that are coupled together by a pre-loaded connection 61. In the illustrated embodiment, the set screw 60 is engaged with the locking-cap 50 via thread patterns 52 and 62, for example. In some embodiments, it may be advantageous to initially couple set screw 60 to locking-cap 50 by a pre-loaded connection 61. An example pre-loaded connection 61 may fixedly couple the set screw 60 to locking-cap 50. Additionally, the pre-loaded connection 61 may be configured to be severed, or otherwise broken, when a sufficient force is applied to set screw 60 relative to connector 50, for example. In at least one embodiment, the pre-loaded connection 61 may comprise at least one tac weld or surface weld at a portion of locking-cap module 100 where set screw 60 and connector 50 contact one another. For example, a precisely sized and dimensioned laser welded seam or laser welded point at a junction between set screw 60 and connector 50 on a bottom surface or on an upper surface. Other embodiments may utilize an adhesive or an epoxy as a functional equivalent. For example, a thread locker may be used in some embodiments. In at least embodiment, the pre-loaded connection 61 may be designed to sustain a maximum force, i.e., the pre-loaded connection may be configured to sever or break at a pre-determined design load. For example, when a sufficient rotational force is applied to set screw 60 relative to locking-cap 50 the pre-loaded connection 61 may sever and the set screw 60 can, thereafter, rotate relative to connector 30 via threads 52, and 62. In at least one embodiment, the pre-loaded connection 61 can sustain a maximum force of about 35 inch lbs., although this number may be adjusted based on the particular design criteria and/or preferences of a surgeon, for example. In another embodiment, the pre-loaded connection can sustain a maximum force of about 15-30 inch lbs. and more particularly about 20 inch pounds. In the illustrated embodiment of FIG. 4B, four pre-loaded connections 61 (laser welds or tac welds) are spaced radially and symmetrically around the edges (seam) where set screw 60 and locking-cap 50 contact one another on an underside of locking-cap module 100, for example. However, in other embodiments, two pre-loaded connections may be spaced radially and symmetrically around the edges (seam) where set screw 60 and locking-cap 50 contact one another on an underside of locking-cap module 100, for example.

Figure 5:
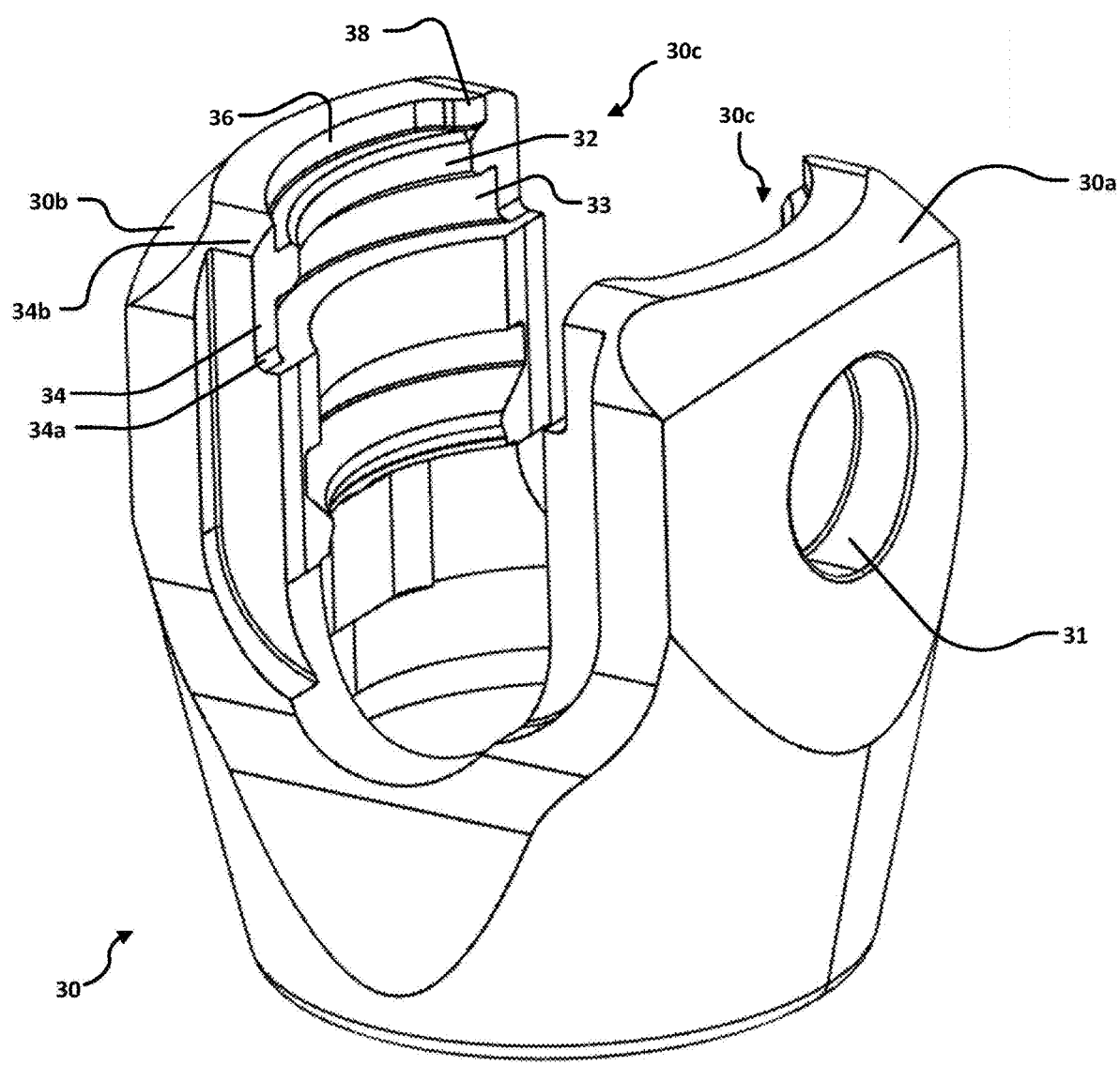
FIG. 5 is a perspective view of an example connector.

FIG. 5 is a perspective view of an example connector 30. In the illustrated embodiment, connector 30 may include a plurality of arm portions 30a, 30b which may define, at least partly, side surface of connector 30. In the example embodiment, a first arm portion 30a and a second arm portion 30b are disclosed. Each arm portion 30a, 30b, may include at least one gripping portion 31 disposed on an exposed side surface of connector 30. The gripping portion 31 may be configured such that a reduction instrument or other surgical tool may rigidly hold onto connector 30 for positioning of the connector 30 and/or to reduce or properly position a longitudinal rod 20 within a rod passageway of connector 30. Each arm portion 30a, 30b may include and/or otherwise define an upper surface of connector 30, at least partly, for example.

Each arm portion 30a, 30b, may include a corresponding connecting portion 30c, for example Each connecting portion 30c may be configured to connect with corresponding features of locking-cap 50, for example. In the illustrated example embodiment, connection portion 30c may be disposed proximate an upper portion of connector 30 on exposed interior side surfaces thereof. Each connecting portion 30c may include a connecting rail 32, a lower channel 33, and an upper channel 36, for example. The connecting rail 32 may protrude laterally from an internal side surface of a corresponding arm portion 30a and 30b, for example, and thereby define the lower channel 33 and upper channel 36. The upper channel 36 may be further defined by and/or considered to include a stopping feature 38, for example. In various embodiments, stopping feature 38 may be a curved outdent, a straight outdent, a planar surface, etc. In some embodiments, the curvature of the stopping feature 38 may correspond to the curvature of an outdent of locking-cap 50, for example, locking edge 58. In practice, stopping feature 38 may directly contact locking edge 58 and prevent locking-cap 50 from rotating past stopping feature 38, for example. Additionally, connector 30 may include a mating cavity 34 for receiving a corresponding mating protrusion 204 of surgical tool 200, for example. Mating cavity 34 may have and/or be defined by a vertically oriented planar surface that adjoins a curved and/or ramped surface 34a at a bottom portion of mating cavity 34. Additionally, mating cavity 34 may adjoin a slanted top surface 34b of the connector 30. As will be explained in further detail below, mating protrusion 204 may be seated within mating cavity 34 and prevent locking-cap 50 from rotating in a counter clockwise direction.

Figure 6A:
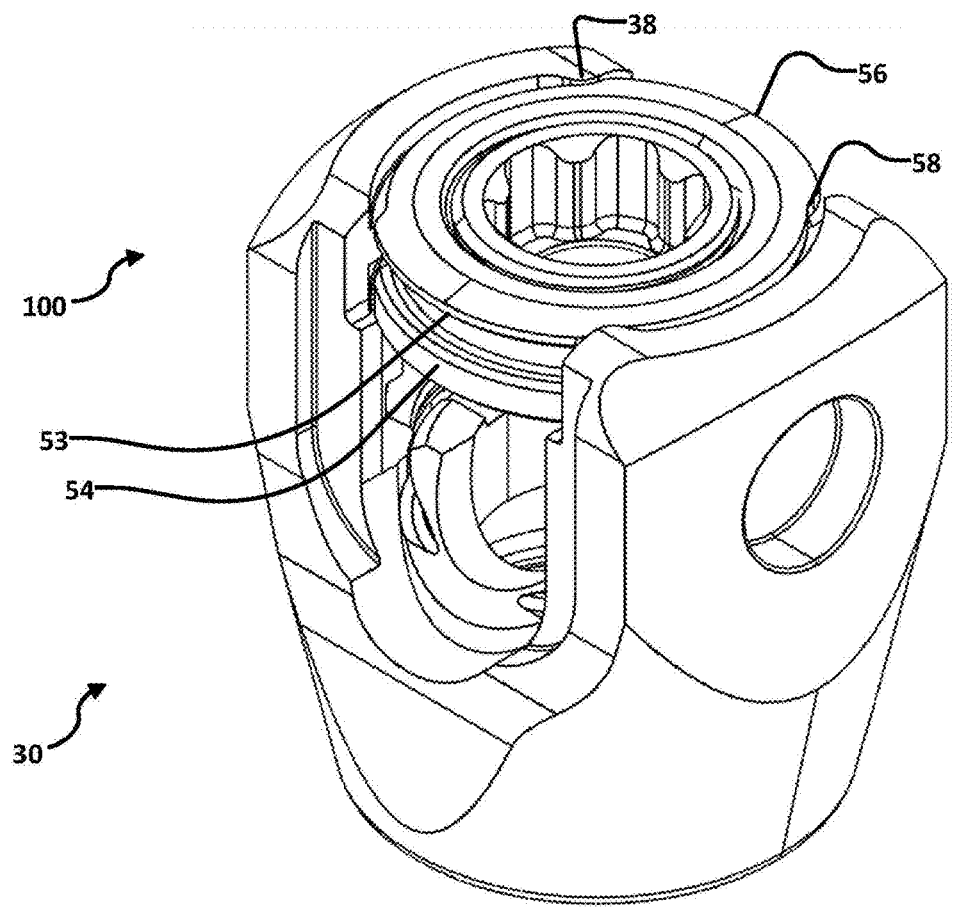
FIG. 6A is a perspective view of an example locking-cap system in an initial position before being engaged in a locking position.
Figure 6B:
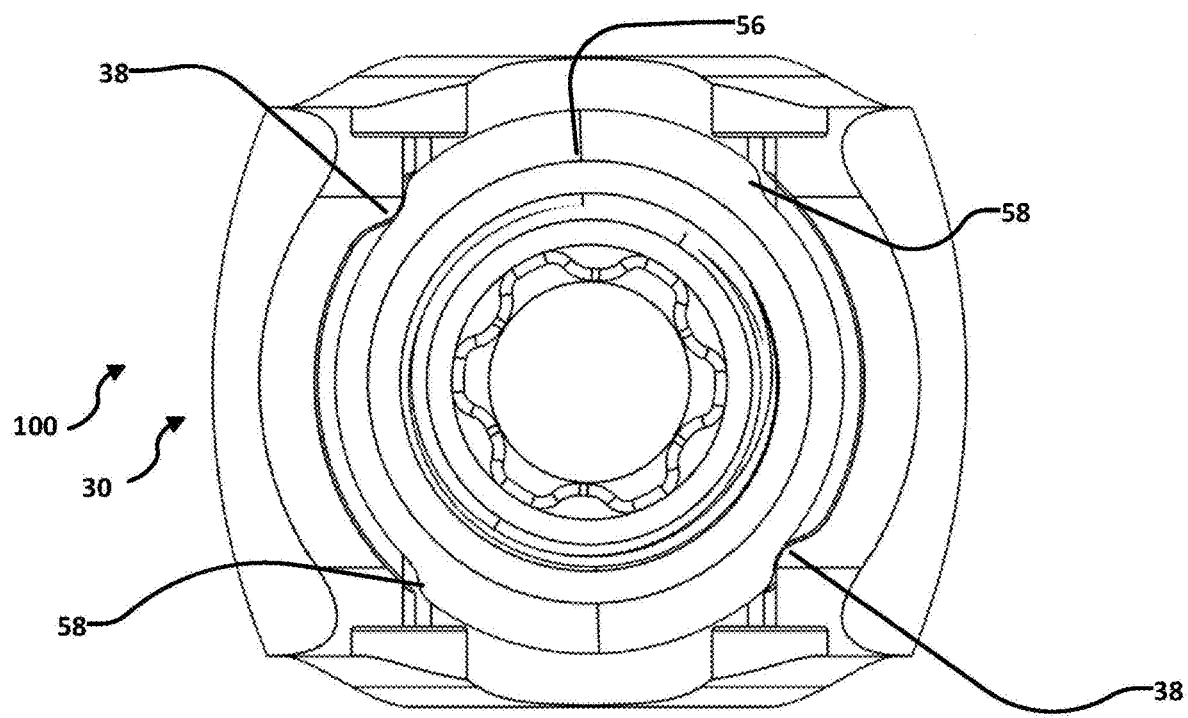
FIG. 6B is a top down view of an example locking-cap system in an initial position before being engaged in a locking position.

FIG. 6A is a perspective view of an example locking-cap module 100 in an initial position (a non-tightened position and/or a non-engaged position) before being engaged in an engaged position (a tightened position). FIG. 6B is a top down view of an example locking-cap module 100 in an initial position before being engaged in a locking position. As illustrated, the locking-cap module 100 is positioned between arms 30a and 30b in an initial position, for example. In the initial position, the rails 54, connecting flanges 56, and locking edge 58 may not be engaged with the connecting portion 30c of connector 30, for example.

Figure 7A:
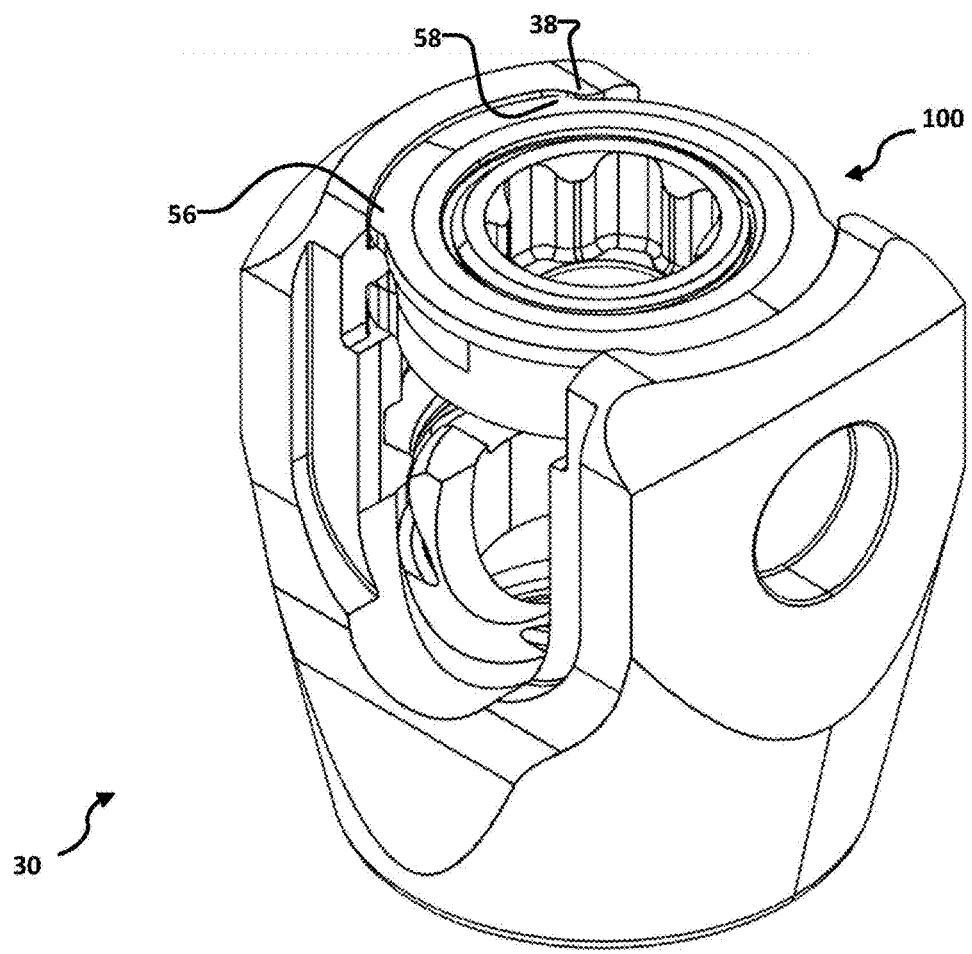
FIG. 7A is a perspective view of an example locking-cap system after being engaged in a locking position.
Figure 7B:
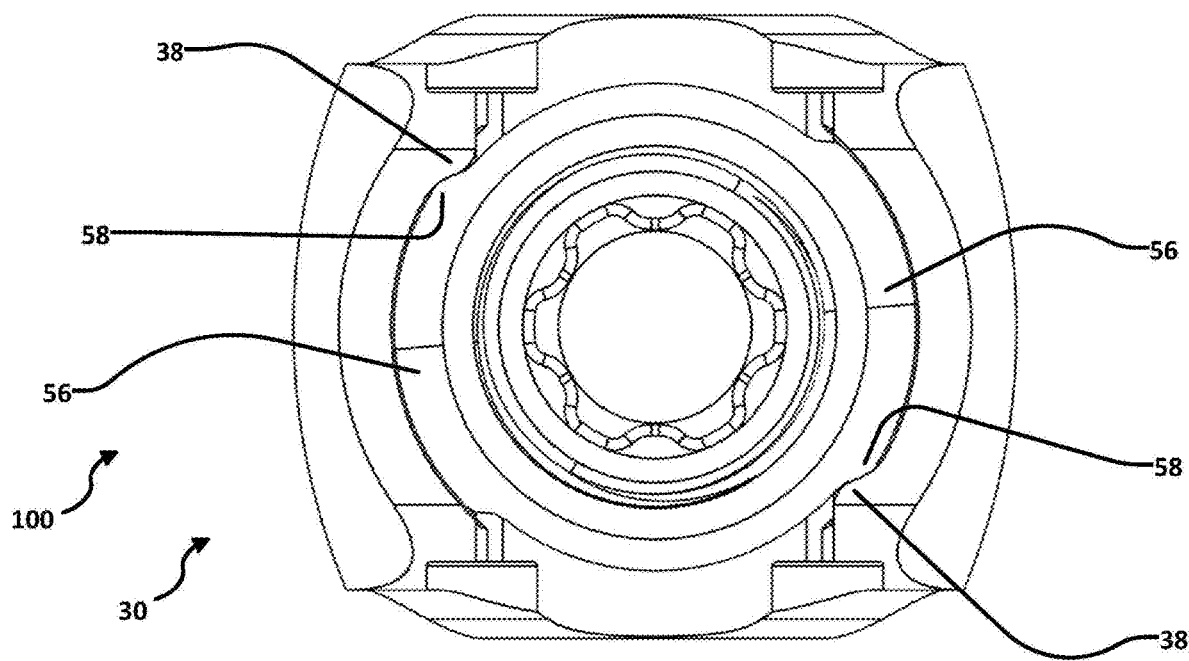
FIG. 7B is a top down view of an example locking-cap system after being engaged in a locking position.

FIG. 7A is a perspective view of an example locking-cap module 100 after being engaged in the locking position. FIG. 7B is a top down view of an example locking-cap module 100 after being engaged in the locking position. As illustrated, the rails 54, connecting flanges 56, and locking edge 58 may be selectively coupled and/or engaged with the connecting portion 30c of connector 30. In the example embodiment, each rail 54 may be mated to and/or positioned within a corresponding lower channel 33 of connector 30 and each connecting flange 56 may be mated to and/or positioned within a corresponding upper channel 36. Furthermore, each locking edge 58 may be mated to and/or stopped from further rotation by stopping feature 38.

In practice, an end user such as a surgeon may first position a pre-loaded locking module 100 in the initial position as shown in FIGS. 6A and 6B. Thereafter, the end user may rotate the locking-cap module 100 clockwise by engaging a driver or a rotation instrument with the drive cavity 64 of set screw 60, for example surgical tool 200 (see FIGS. 12-14). As previously explained, the locking-cap 50 and set screw 60 may be initially coupled by a pre-loaded connection 61. Therefore, by applying a rotational force to set screw 60 the locking-cap module 100 (including the locking-cap 50 and set screw 60) may be positioned in the locking position. In some embodiments, just before fully positioning the locking-cap module 100 in the locking position, the locking-cap module 100, via the locking edge 58 may contact the stopping feature 38 and experience rotational resistance preventing the locking-cap module 100 from further rotating. Afterwards, an end user may continue to apply a rotational force to set screw 60 that is sufficient to overcome the pre-loaded connection 61. Once the pre-loaded connection 61 is broken or otherwise severed, an end user may continue to advance set screw 60 downward along axis A-A towards a longitudinal rod 20 (not illustrated in FIGS. 7A and 7B) while locking-cap 50 stays in place. The locking-cap 50 may be prevented from further rotation due to a stopping feature 38, for example. Stopping feature 38 may protrude from connector 30 towards axis A-A, for example.

Due to the stopping feature 38, the locking-cap 50 may be prevented from further rotating out of the engaged position. Additionally, by continuing to apply a rotational force to set screw 60 in a clockwise direction, the pre-loaded connection 61 between set screw 60 and locking-cap 50 may be overcome and/or broken, for example. After the pre-loaded connection between set screw 60 and locking-cap 50 is broken, an end user may continue to rotate set screw 60 and advance set screw 60 along axis A-A until it directly contacts a longitudinal rod 20 positioned thereunder. In doing so, the locking-cap 50 may securely retain the set screw 60 relative to connector 30 and the set screw 60 may securely retain a longitudinal rod 20 relative to connector 30. Furthermore, if the end user or surgeon needed to reposition the longitudinal rod 20, the end user may back the set screw 60 out due to the locking-cap 50 being seated in the engaged position and prevented from rotating out of the engaged position in a counter clockwise direction due to mating protrusion 204 of surgical tool 200 being seated in the corresponding mating cavity 34 and the pre-loaded connection 61 being broken.

Additionally, in some embodiments, the thread pattern 52 of the locking-cap 50 and/or the thread pattern 62 of the set screw 60 may include a run out portion 62a where the threads and/or the thread pitch terminates or runs out, for example. In some embodiments, the run out portion 62a may be configured to prevent the set screw 60 from threading through the locking-cap 50. Additionally, in some embodiments, the run out portion 62a may also be configured to maintain the set screw 60 in an optimal position to retain the longitudinal rod 20 within the rod passageway of the connector 30.

Figure 8:
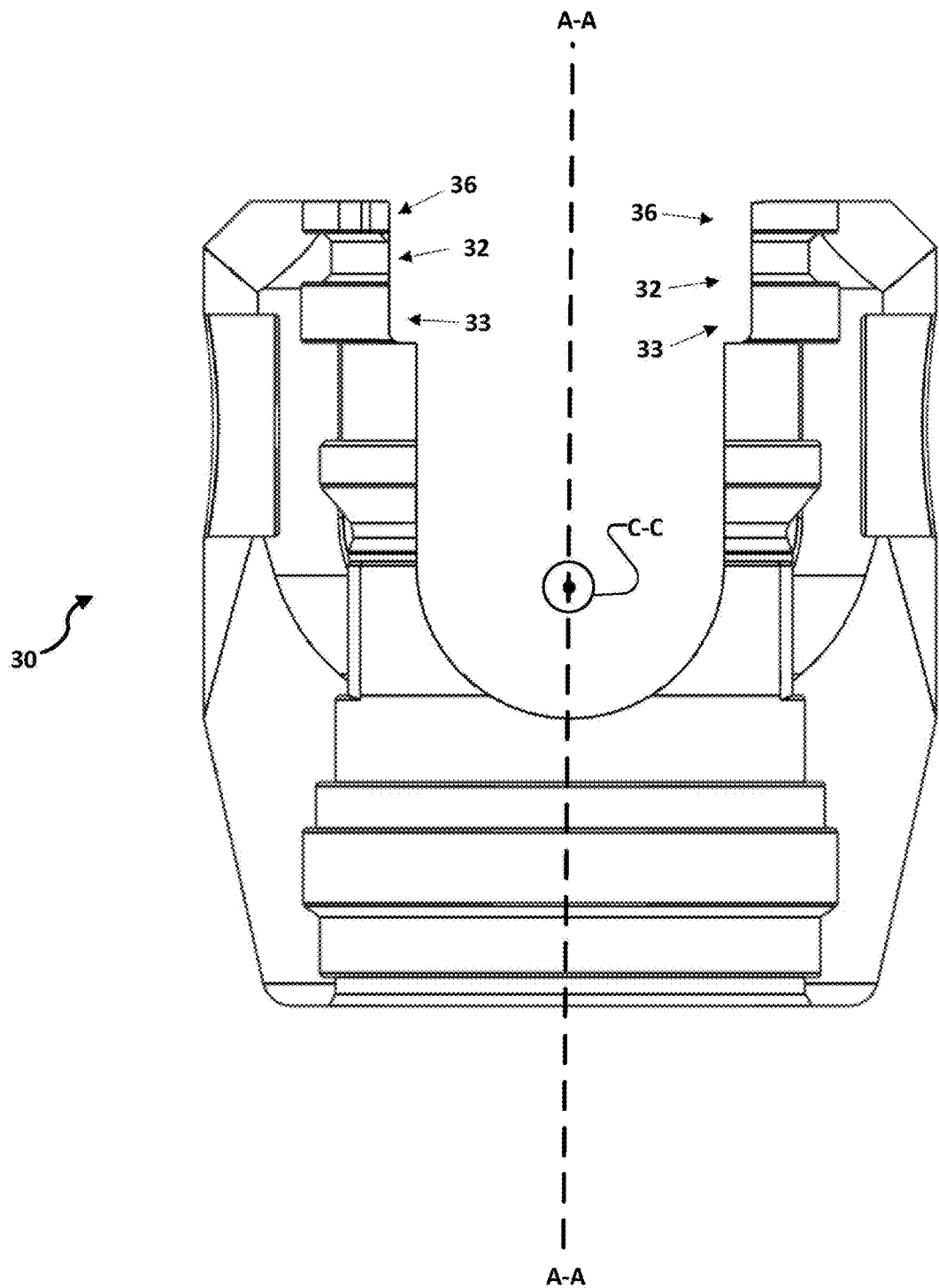
FIG. 8 is a cross sectional view of an example connector.

FIG. 8 is a cross sectional view of an example connector 30. In the example embodiment of FIG. 8, connector 30 is shown in cross section to further illustrate connecting rail 32 being disposed between the lower connecting channel 33 and upper connecting channel 36. Additionally, connector 30 may define a rod passageway configured to orient a longitudinal rod 20 along axis C-C. Consistent with the above disclosure, axis C-C may be further defined by the combination of connector 30, crown 40, and locking-cap 50. It shall also be understood that the specific location of axis C-C is not shown to scale and the exact location of axis C-C relative to connector 30 may be different, i.e., axis C-C is shown only for illustrative purposes. Furthermore, when the longitudinal rod 20 is placed in the rod passageway, axis B-B defined by the longitudinal rod itself may be coextensive with axis C-C defined by connector 30 and locking-cap 50, for example.

Figure 9:
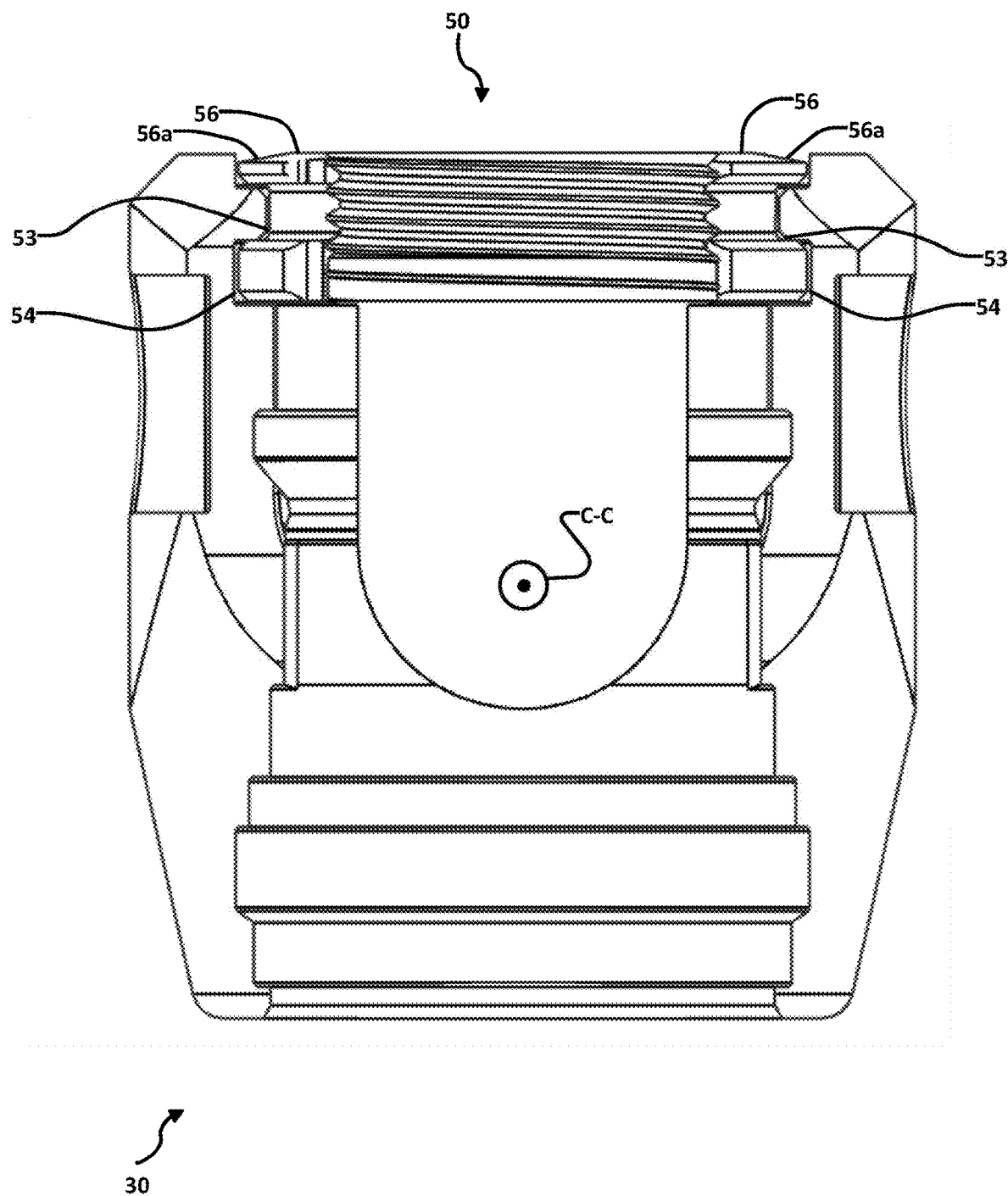
FIG. 9 is a cross sectional view of an example connector and an example locking-cap engaged in a locking position.

FIG. 9 is a cross sectional view of an example connector 30 and an example locking-cap 50 engaged in a locking position. In the example embodiment of FIG. 9, connector 30 and locking-cap 50 are shown in cross section to illustrate flanges 56 being seated within the upper connecting channel 36 and rails 54 being seated within the lower connecting channel 33, for example. As illustrated, flanges 56 may include a substantially flat or planar upper surface that transitions to a slanted surface 56a, for example. In the example embodiment, an uppermost surface of flange 56 is coextensive with an upper surface of connector 30 and an outermost edge of slanted surface 56a is disposed below the upper surface of connector 30. Additionally, it is shown that connecting rail 32 of connector 30 is seated between flanges 56 and rails 54 in the recessed portion 53, for example.

Figure 10:
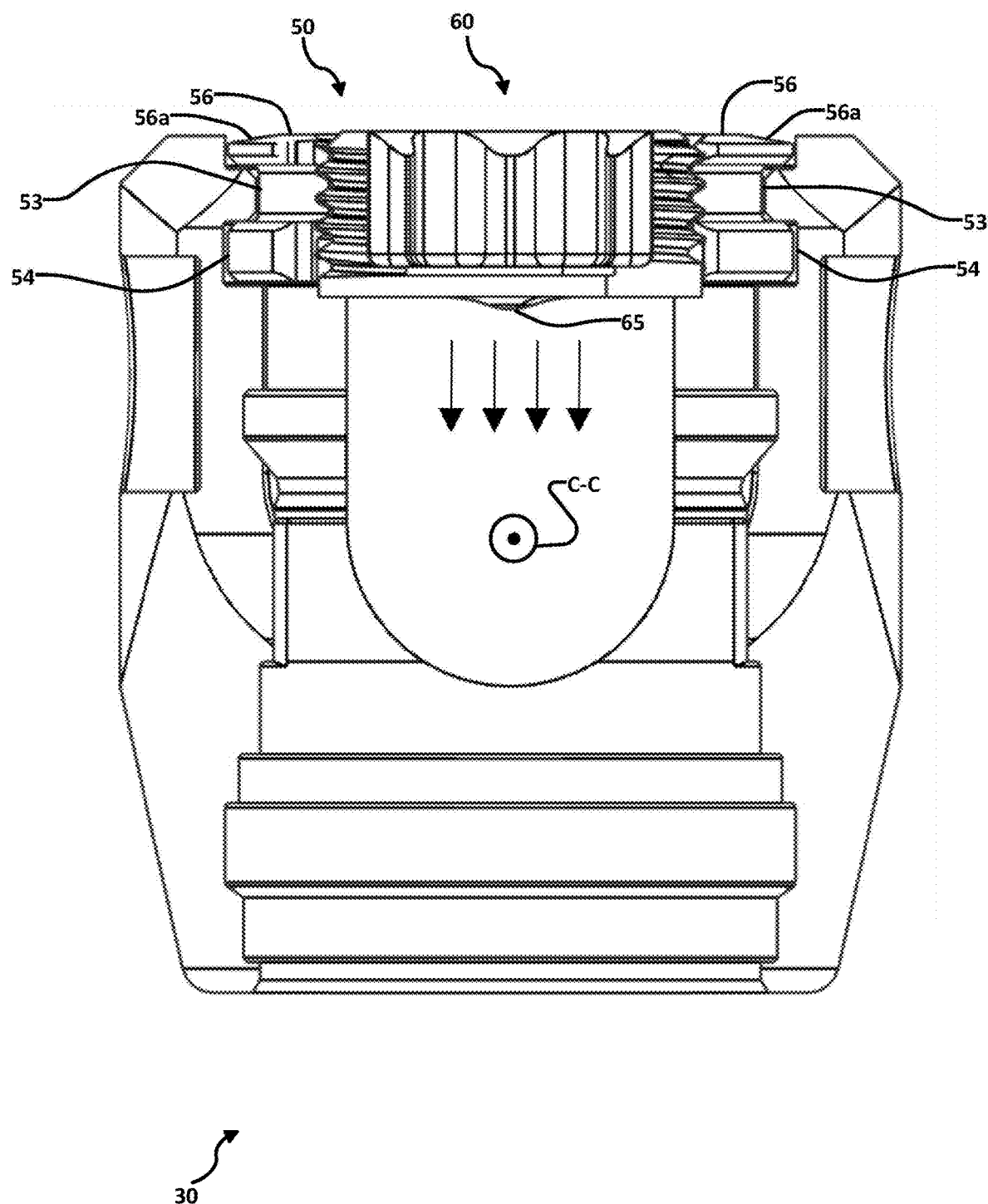
FIG. 10 is a cross sectional view of an example connector, an example locking-cap, and an example set screw engaged in a locking position.

FIG. 10 is a cross sectional view of an example connector 30, an example locking-cap 50, and an example set screw 60 engaged in a locking position. As illustrated, set screw 60 may rotated within locking-cap 50 and advance towards axis C-C. Set screw 60 may apply a downward force (represented by arrows) against a longitudinal rod 20 (not illustrated) that is axially aligned with axis C-C. When set screw 60 is sufficiently tightened against longitudinal rod 20 and applies a downward compressive force against longitudinal rod 20 a return force may be applied upward through set screw 60 and connector 50 at the junction between a top surface of the lower rail 54 of locking-cap 50 and a bottom surface of the rail 32 of connector 30, for example. When the set screw 60 is fully tightened against the longitudinal rod 20 and the locking-cap 50 is in the engaged position, the locking-cap 50 may be considered to be in a locked position as it is prevented from rotating clockwise and counterclockwise due to the transfer of forces as described herein.

Consistent with the above disclosure, the locking-cap 50 may enable the set screw 60 to apply a sufficient downward retaining force against a longitudinal rod 20 while also maintaining a relatively low total height of connector 30. For example, connector 30 may about 11 mm to about 15 mm and more particularly about 13.5 mm in height whereas other connectors relying on threads as opposed to locking-caps may be relatively greater in height. As the set screw 60 is tightened and force is applied as explained above, the locking-cap 50 may experience forces that could cause it to bend, flex, or bow. However, due to an uppermost surface of the flanges 56 being seated flush with the top surface of connector 30 and the geometry of slanted surface 56a the locking-cap 50 may be prevented from bending, flexing, or bowing. In experimental testing, this arrangement has been shown to exhibit relatively significant strength improvements over other designs due to the flanges 56 being constrained laterally and therefore unable to bend, bow, or flex.

Figure 11A:
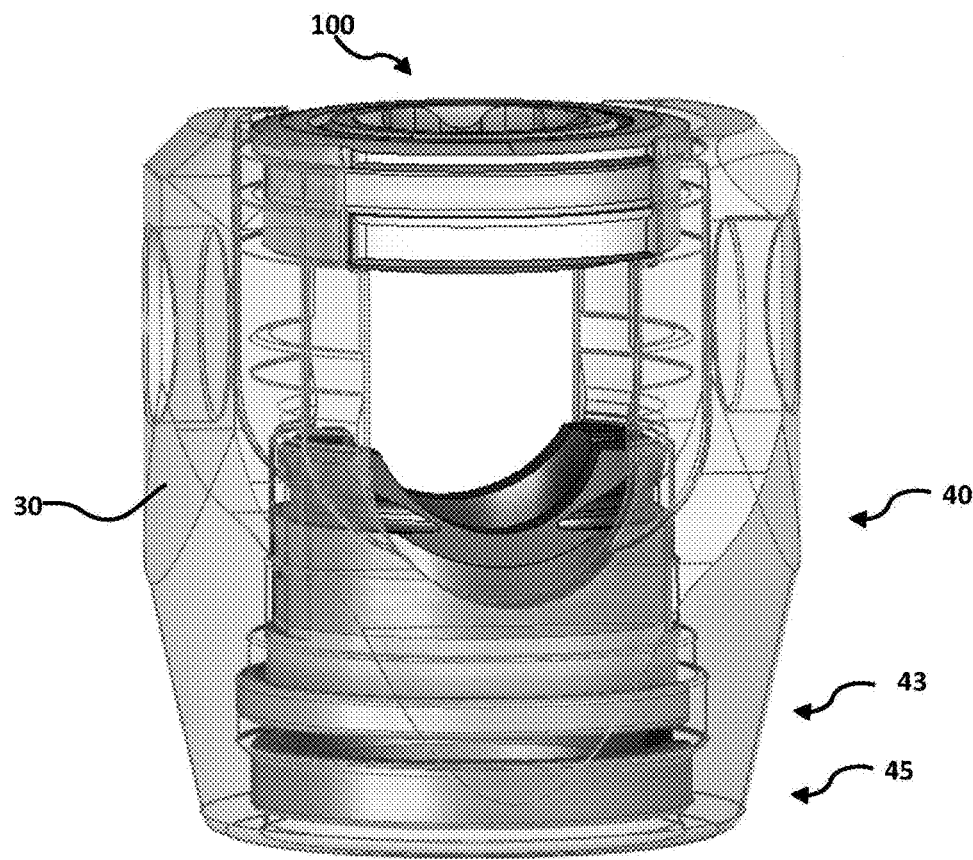
FIG. 11A is a transparent view with shading of an example locking-cap system in an initial position before being engaged in a locking position.
Figure 11B:
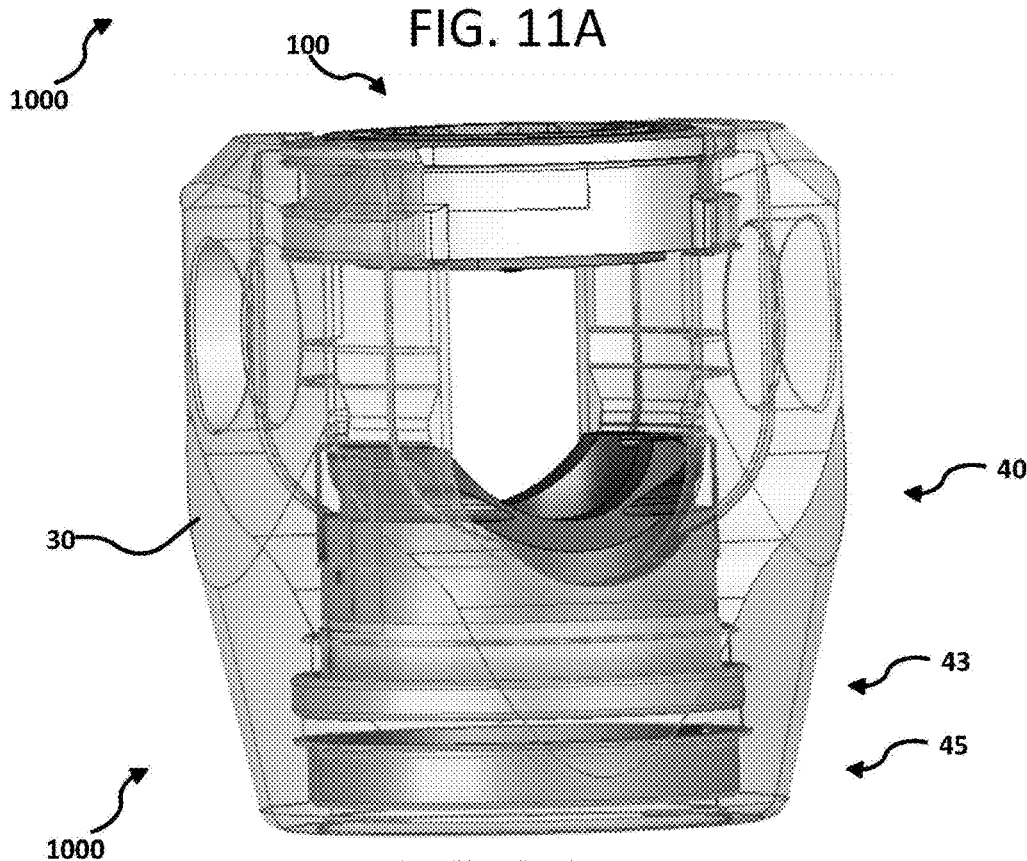
FIG. 11B is a transparent view with shading of an example locking-cap system in an engaged position.

FIG. 11A is a transparent view with shading of an example locking-cap system 1000 in an initial position before being engaged in a locking position, for example. FIG. 11B is a transparent view with shading of an example locking-cap system 1000 in an engaged position, for example. In the transparent view, it is shown how locking-cap module 100 is retained by an upper portion of connector 30 and how crown 40, washer 43, and washer 45 are secured in a lower portion of connector 30. Consistent with the disclosure herein, it shall be understood that a head portion of anchoring member 10 (not illustrated in FIGS. 11A and 11B) may also be positioned in the lower portion of connector 30.

Figure 12A:
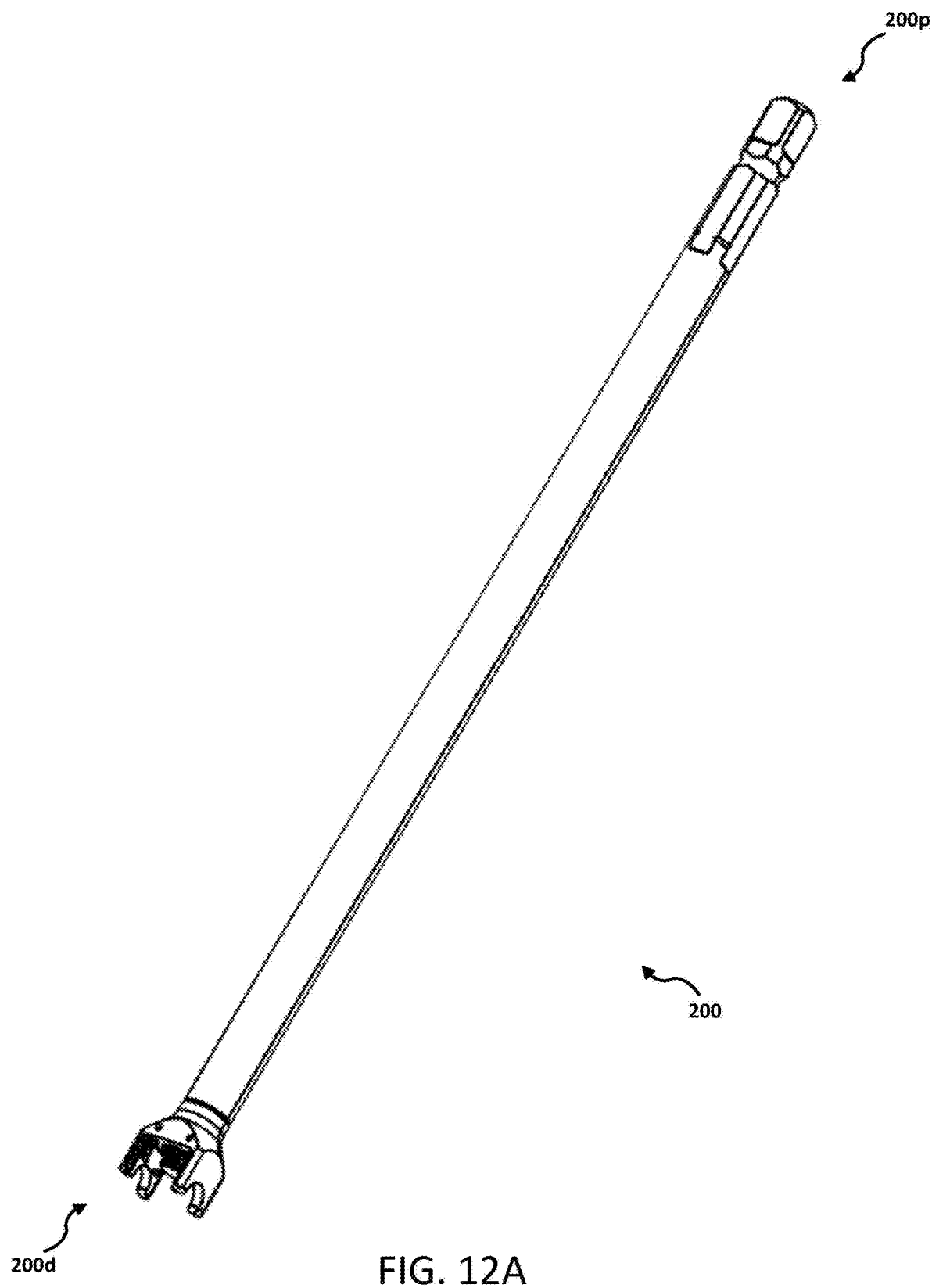
FIG. 12A is a perspective view of an example surgical tool for use with disclosed locking-cap systems.
Figure 12B:
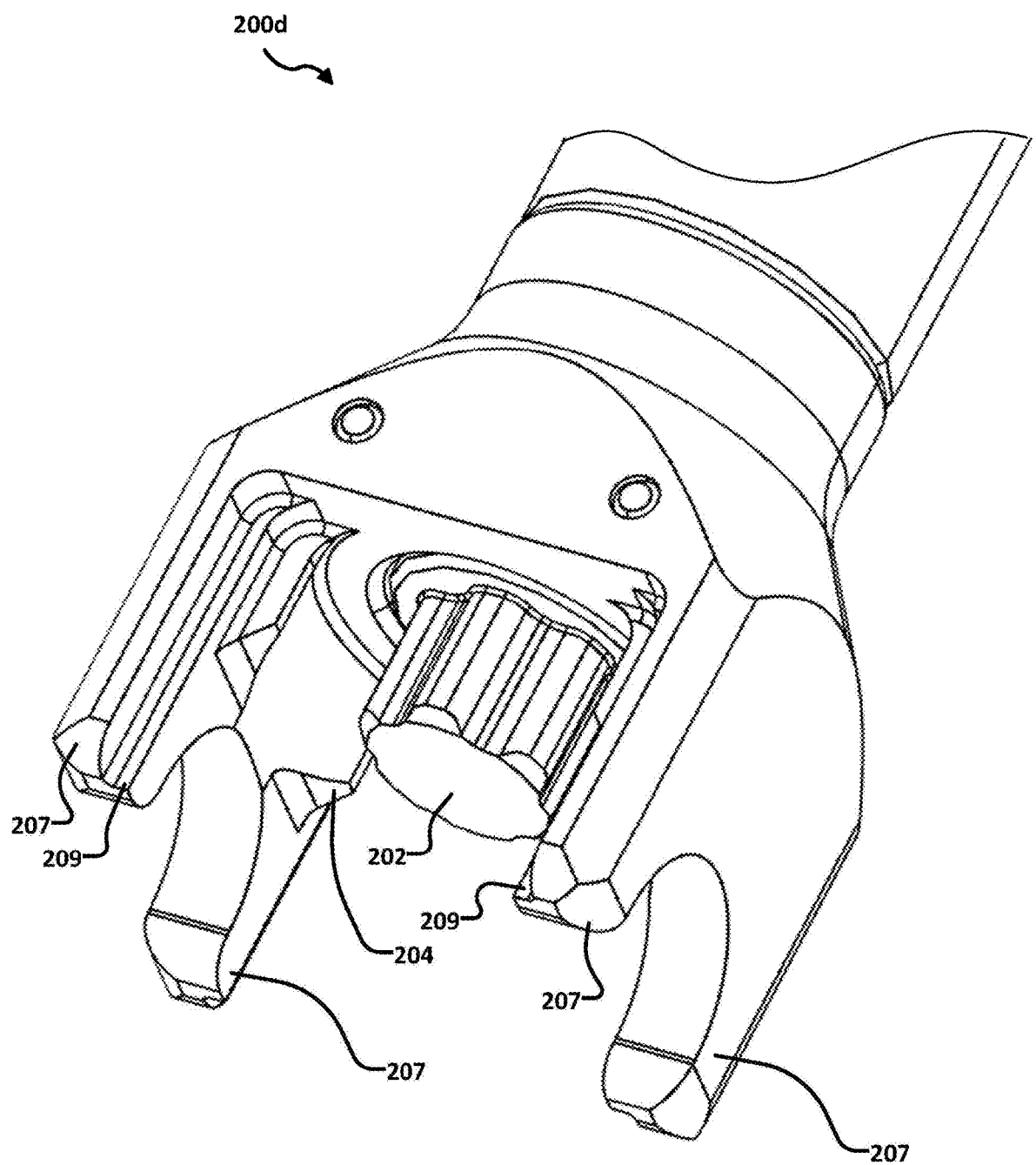
FIG. 12B is an enlarged perspective view of a distal end of the surgical tool of FIG. 11.

FIG. 12A is a perspective view of an example surgical tool 200 for use with disclosed locking-cap systems 1000. Surgical tool 200 may include a proximal end 200p and a distal end 200d. At the proximal end 200p a drive end 205 is illustrated, for example Drive end 205 may be coupled to a hand driver (not illustrated) or a powered driver, for example FIG. 12B is an enlarged perspective view of a distal end 200d of surgical tool 200. In the example embodiment, surgical tool 200 may have four arms 207, for example. A pair of adjacent arms 207 may define a slotted aperture therebetween, for example. The slotted aperture may be configured to seat around a longitudinal rod 20 and have a size and shape generally corresponding to the side surface of the longitudinal rod 20, for example. Each arm 207 may extend in a longitudinal direction with respect to surgical tool 200. Similarly, each arm 207 may have a mating rail 209 extending in a longitudinal direction with respect to surgical tool 200 and protruding inward from arm 207 towards drive feature 202, for example. Additionally, surgical tool 200 may include a drive feature 202 at a distal end 200d. In operation, the drive end 205 may be rotated which in turn rotates drive feature 202. Therefore, when drive feature 202 is mated with drive cavity 64 of set screw 60, drive feature 202 may rotate locking module 100 via set screw 60 and the pre-loaded connection 61, for example. Additionally, drive feature 202 may continue to rotate set screw 60 after the pre-loaded connection 61 is broken.

Figure 13:
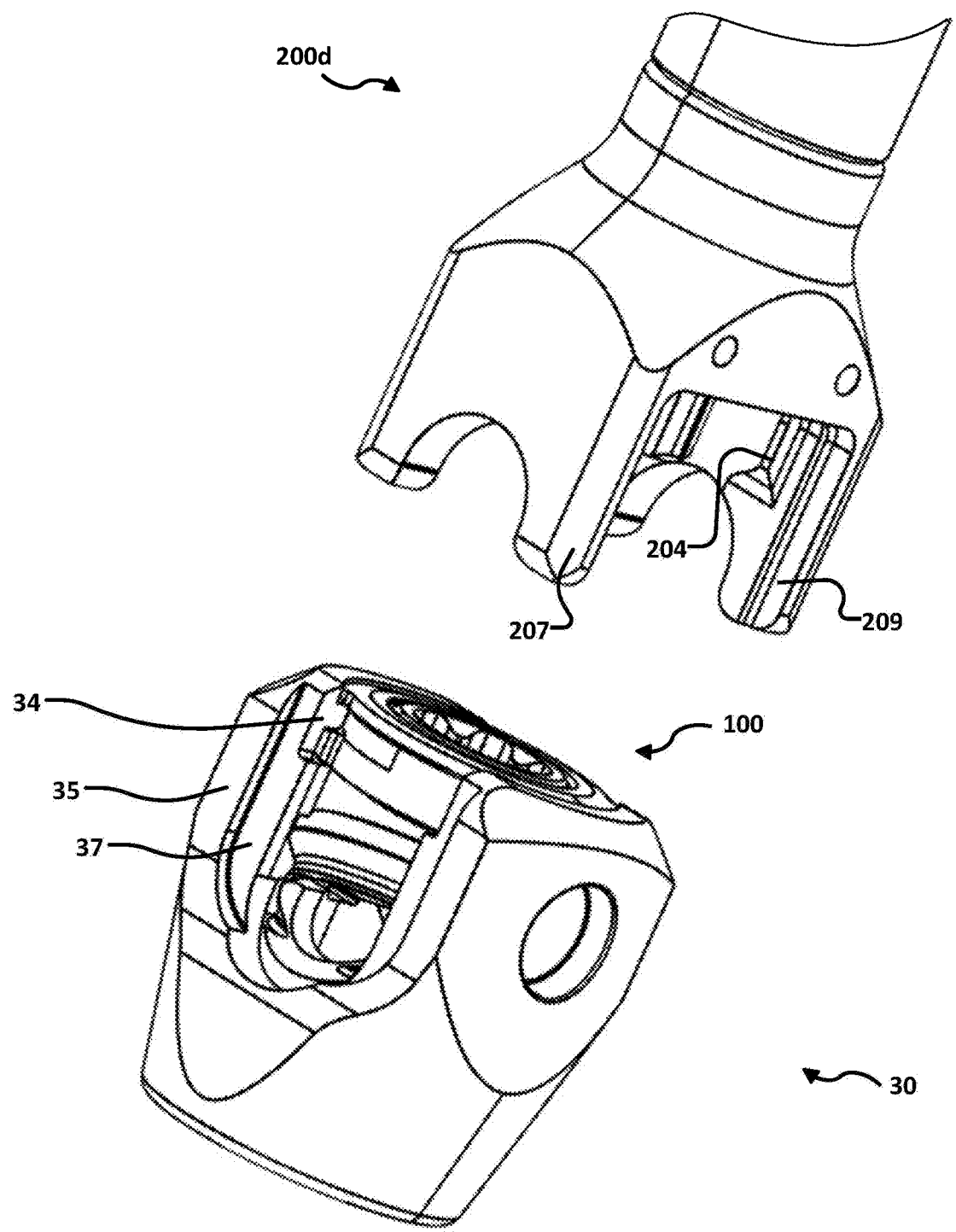
FIG. 13 is an enlarged perspective view showing the surgical tool of FIG. 11 and an example locking module in an uncoupled position.
Figure 14:
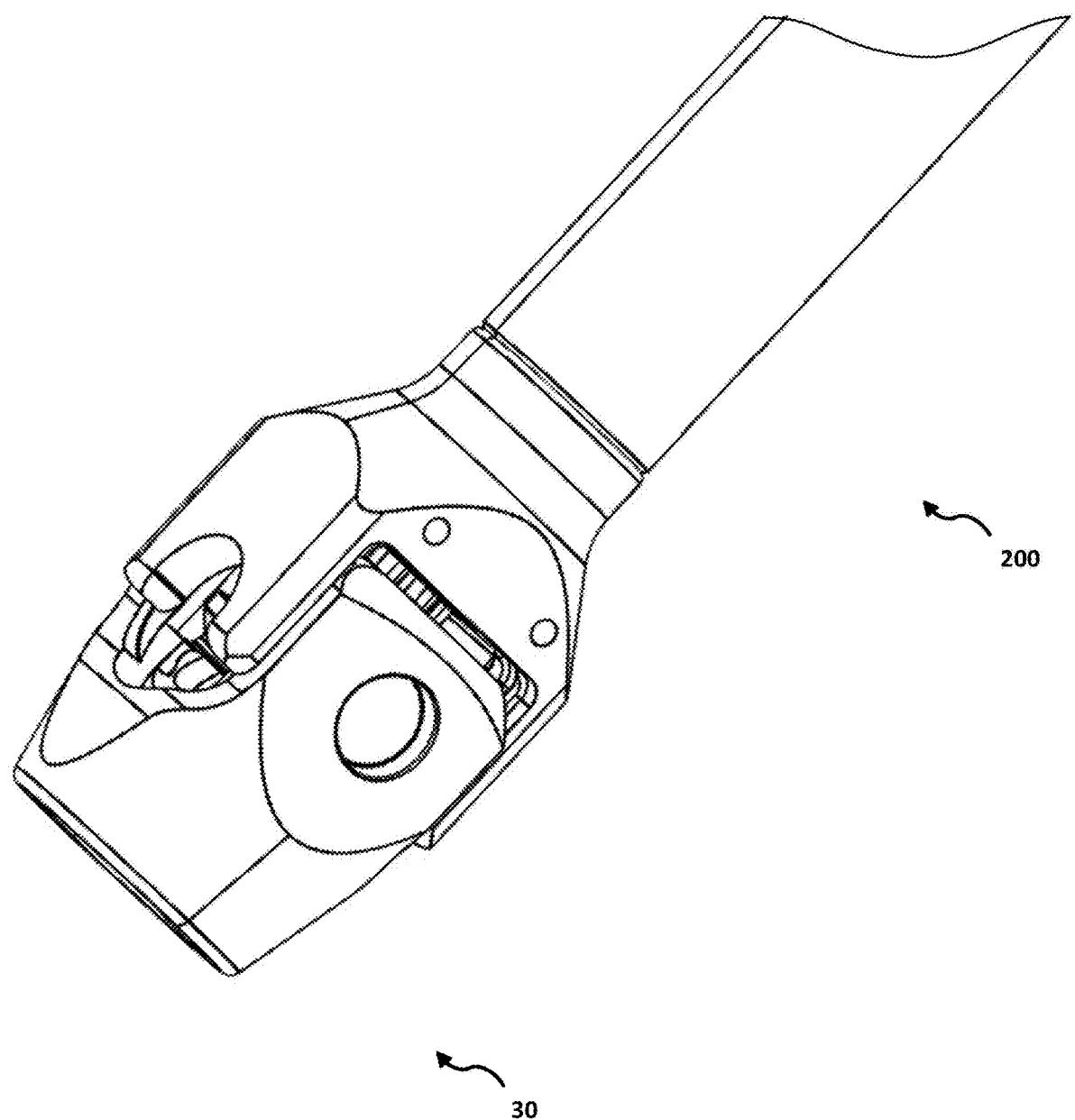
FIG. 14 is an enlarged perspective view showing the surgical tool of FIG. 11 and an example locking module in coupled position.

FIG. 13 is an enlarged perspective view showing the surgical tool 200 and an example locking module 100 and connector 30 in an uncoupled position. As illustrated, surgical tool 200 includes a plurality of mating protrusions 204, for example. In the example embodiment, four mating protrusions 204 are provided. FIG. 14 is an enlarged perspective view of surgical tool 200 and an example locking module 100 and connector 30 in a coupled position. In the coupled position, mating protrusions 204 may be seated within mating cavity 34, for example. In various embodiments, mating protrusions 204 may have a size and shape generally corresponding to a size and shape corresponding to mating cavity 34, for example Additionally, in the coupled position, arms 207 may surround connector 30 and directly contact lateral sidewalls 35, for example. In the example embodiment, lateral sidewalls 35 are planar surfaces that extend in a longitudinal direction of connector 30, for example. Furthermore, in the coupled position, mating rail 209 may be seated within mating channel 37, for example.

In the coupled position, the structural arrangement of mating rail 209 and mating channel 37 and arms 207 and lateral side surfaces 35 may provide a counter torque to prevent connector 30 from rotating when driving set screw 60, for example Additionally, in the coupled position, the structural arrangement of mating protrusion 204 and mating cavity 34 may prevent locking-cap 50 from moving out of the engaged position. For example, in the event an end user needs to back the set screw 60 out and away from longitudinal rod 20 by rotating drive feature 202 in a counter clockwise direction, mating protrusion 204 may prevent locking-cap 50 from also rotating in the counter clockwise direction. Accordingly, surgical tool 200 may provide a counter torque to locking-cap 50 via mating protrusions 204 being seated within mating cavity 34. For example, an end surface of flanges 56 and/or rail 54 may contact mating protrusion 204 and be prevented from rotating relative to connector 30.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A locking-cap module, comprising:
    a locking-cap including:
        an internal circumferential surface having a first thread pattern; and
        a first connecting flange and a second connecting flange opposite the first connecting flange, the first and second connecting flanges extending from a side surface of the locking-cap and defining, at least partly, a top surface of the locking-cap; and
        a first retaining rail and a second retaining rail opposite the first retaining rail, the first and second retaining rails extending from the side surface of the locking-cap and defining, at least partly, a bottom surface of the locking-cap; and
    a set screw including an external circumferential surface having a second thread pattern, the second thread pattern corresponding in size and shape to the first thread pattern for mating with the first thread pattern;
    wherein the locking-cap is configured to be transitioned from an unengaged position relative to an external connector to an engaged position relative to the external connector, when the locking-cap module is in use; and
    wherein both the top surface of the locking-cap and the top surface of the set screw are level with a top surface of the connector when the locking-cap is in the unengaged position relative to the external connector; and
    wherein the locking-cap is configured such that (i) the top surface of the locking-cap remains level with the top surface of the external connector and (ii) the top surface of the set screw becomes unlevel with the top surface of the connector when torque is applied to the set screw after the locking-cap has transitioned to the engaged position relative to the external connector.

2. The locking-cap module of claim 1, wherein the first connecting flange includes a first locking edge and the second connecting flange includes a second locking edge.

3. The locking-cap module of claim 2, wherein the first locking edge comprises a first outdent and the second locking edge comprises a second outdent.

4. The locking-cap module of claim 3, wherein, in the engaged position, the first locking edge is engaged with a first stopping feature of the external connector and the second locking edge is engaged with a second stopping feature of the external connector.

5. The locking-cap module of claim 4, wherein:
    the first connecting flange comprises a first slanted surface and the second connecting flange comprises a second slanted surface, and
    in the engaged position, the first slanted surface and the second slanted surface are disposed below the upper surface of the external connector.

6. The locking module of claim 1, wherein the set screw and the locking-cap are initially coupled together by a pre-loaded connection.

7. The locking-cap module of claim 6, wherein:
    the pre-loaded connection of the set screw and locking-cap is configured to allow the locking-cap to be tightened into the engaged position by engaging and rotating the set screw, and
    after the locking-cap is in the engaged position, the pre-loaded connection of the set screw and locking-cap is configured to break upon applying a sufficient rotational force to overcome the pre-loaded connection.

8. The locking-cap module of claim 7, wherein the first thread pattern comprises a counterbore and the second thread pattern comprises a run-out-portion.

9. The locking-cap module of claim 8, wherein the run-out-portion is configured to maintain the set screw at a position in which the set screw captures and retains a longitudinal rod extending through a rod passageway of the connector.

10. A locking-cap system, comprising:
    a locking-cap including:
        an internal circumferential surface having a first thread pattern;
        a first connecting flange and a second connecting flange opposite the first connecting flange, the first and second connecting flanges extending from a side surface of the locking-cap and defining, at least partly, a top surface of the locking-cap; and a first retaining rail and a second retaining rail opposite the first retaining rail, the first and second retaining rails extending from the side surface of the locking-cap and defining, at least partly, a bottom surface of the locking-cap;

a set screw including an external circumferential surface having a second thread pattern, the second thread pattern corresponding in size and shape to the first thread pattern for mating with the first thread pattern;

a connector including:

an internal surface comprising a rod passageway and a connecting portion, the connecting portion disposed proximate an upper surface of the connector and configured to selectively couple with the locking-cap such that the locking-cap is fixed relative to the connecting portion in an engaged position, the connecting portion including:

a first connecting channel and a second connecting channel opposite the first connecting channel, the first connecting channel being configured to connect with the first connecting flange and the second connecting channel being configured to connect with the second connecting flange;

a third connecting channel and a fourth connecting channel opposite the third connecting channel, the third connecting channel being configured to connect with the first retaining rail and the fourth connecting channel being configured to connect with the second retaining rail;

a surgical tool comprising a distal end with (i) a plurality of arms configured to engage with a plurality of lateral sidewalls of the connector to provide a counter-torque to the connector and (ii) with a plurality of mating rails configured to engage with a plurality of mating channels of the connector to provide counter-torque to the connector; and wherein, when the locking-cap is in the engaged position, the first connecting flange and the second connecting flange engage with the connector such that an uppermost surface of the first connecting flange and an uppermost surface of the second connecting flange are generally flush with a top surface of the connector.

11. The locking-cap system of claim 10, wherein:

the first connecting flange has a first locking edge and the second connecting flange has a second locking edge, and the connector has a first stopping feature and a second stopping feature, the first stopping feature being configured to engage with the first locking edge for preventing the locking-cap from rotating out of the engaged position and the second stopping feature being configured to engage with the second locking edge for preventing the locking-cap from rotating out of the engaged position.

12. The locking-cap system of claim 11, wherein the a proximal end of the surgical tool has a rotatable drive feature configured to engage with a drive cavity of the set screw.

13. The locking-cap system of claim 10, wherein the set screw and the locking-cap are initially coupled together by a pre-loaded connection.

14. The locking-cap system of claim 13, wherein:

the pre-loaded connection of the set screw and locking-cap is configured to allow the locking-cap to be tightened into the engaged position by engaging and rotating the set screw, and after the locking-cap is in the engaged position, the pre-loaded connection of the set screw and locking-cap is configured to break upon applying a sufficient rotational force to overcome the pre-loaded connection.

15. The locking-cap system of claim 14, wherein the first thread pattern comprises a counterbore and the second thread pattern comprises a run-out-portion.

16. The locking-cap system of claim 15, further comprising:

a longitudinal rod;

a crown;

an anchoring member;

wherein the connector is secured to the anchoring member, wherein the longitudinal rod extends through the rod passageway, wherein the crown facilitates positioning of the longitudinal rod in the rod passageway, and wherein the run-out-portion is further configured to maintain the set screw at a position in which the set screw captures and retains the longitudinal rod within the rod receiving passageway.

17. A method for engaging a two piece locking-cap module with a connector, the method comprising:

providing a locking module comprising a locking-cap and a set screw, the set screw being operably coupled with the locking-cap by a preloaded connection, the locking-cap including:

a first connecting flange and a second connecting flange opposite the first connecting flange, the first and second connecting flanges extending from a side surface of the locking-cap and defining, at least partly, a top surface of the locking-cap;

a first retaining rail and a second retaining rail opposite the first retaining rail, the first and second retaining rails extending from the side surface of the locking-cap and defining, at least partly, a bottom surface of the locking-cap;

providing a connector, the connector including:

an internal surface comprising a rod passageway and a connecting portion, the connecting portion disposed proximate an upper surface of the connector and configured to couple with the locking-cap such that the locking-cap is fixed relative to the connecting portion in an engaged position, the connecting portion including:

a first connecting channel and a second connecting channel opposite the first connecting channel, the first connecting channel being configured to connect with the first connecting flange and the second connecting channel being configured to connect with the second connecting flange;

a third connecting channel and a fourth connecting channel opposite the third connecting channel, the third connecting channel being configured to connect with the first retaining rail and the fourth connecting channel being configured to connect with the second retaining rail;

providing a surgical tool having a proximal end including a drive end and a distal end including a rotatable drive feature, a plurality of arms and a plurality of mating rails;

engaging the drive feature with a drive cavity of the set screw;

rotating the locking-cap module, via the drive cavity of the set screw, into the engaged position thereby fixing the locking-cap relative to the connector such that an upper surface of the first connecting flange and an upper surface of the second connecting flange are generally flush with corresponding upper surfaces of the connector, respectively;

rotating the set screw, after the locking-cap is fixed relative to the connector, with sufficient force to overcome the pre-loaded connection; and providing a counter-torque to the connector via engagement of (i) the plurality of arms of the surgical tool with a plurality of lateral sidewalls of the connector and (ii) the plurality of mating rails of the surgical tool with a plurality of mating channels of the connector.

18. The method of claim 17, further comprising:

installing an anchoring member in a boney structure of a patient;

securing the connector to the anchoring member;

positioning a crown within the connector;

positioning a longitudinal rod within a rod passageway of the connector on top of the crown; and rotating the set screw, after overcoming the pre-loaded connection, thereby securing the longitudinal rod with the rod passageway.

* * * * *